United States Patent
Jaffee et al.

(10) Patent No.: US 10,398,764 B2
(45) Date of Patent: Sep. 3, 2019

(54) ANNEXIN A2 AS IMMUNOLOGICAL TARGET

(71) Applicant: The Johns Hopkins University, Baltimore, MD (US)

(72) Inventors: Elizabeth Marion Jaffee, Lutherville, MD (US); Lanqing Huang, Ellicott City, MD (US); Lei Zheng, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/249,534

(22) Filed: Apr. 10, 2014

(65) Prior Publication Data

US 2014/0227286 A1 Aug. 14, 2014

Related U.S. Application Data

(63) Continuation of application No. 13/132,509, filed as application No. PCT/US2009/066374 on Dec. 2, 2009, now abandoned.

(60) Provisional application No. 61/119,537, filed on Dec. 3, 2008.

(51) Int. Cl.
| | |
|---|---|
| *G01N 33/50* | (2006.01) |
| *C07K 16/30* | (2006.01) |
| *A61K 39/395* | (2006.01) |
| *G01N 33/53* | (2006.01) |
| *A61K 39/00* | (2006.01) |
| *C07K 16/18* | (2006.01) |
| *A61K 38/19* | (2006.01) |
| *G01N 33/68* | (2006.01) |
| *A61K 38/00* | (2006.01) |

(52) U.S. Cl.
CPC ........ *A61K 39/0011* (2013.01); *A61K 38/193* (2013.01); *A61K 39/0005* (2013.01); *A61K 39/39558* (2013.01); *C07K 16/18* (2013.01); *C07K 16/303* (2013.01); *G01N 33/5011* (2013.01); *G01N 33/6893* (2013.01); *A61K 38/00* (2013.01); *A61K 2039/505* (2013.01); *A61K 2039/575* (2013.01); *C07K 2317/73* (2013.01); *G01N 2333/4724* (2013.01); *G01N 2500/04* (2013.01); *G01N 2500/10* (2013.01); *G01N 2800/52* (2013.01)

(58) Field of Classification Search
None
See application file for complete search history.

(56) References Cited

U.S. PATENT DOCUMENTS

| 6,350,445 | B1 | 2/2002 | Jaffee et al. |
|---|---|---|---|
| 7,625,868 | B2 | 12/2009 | Sharma et al. |
| 7,854,932 | B2 | 12/2010 | Singh |
| 2003/0152923 | A1 | 8/2003 | Yakhini et al. |
| 2003/0170235 | A1* | 9/2003 | Cohen .............. A61K 39/39558 424/143.1 |
| 2005/0136059 | A1* | 6/2005 | Thorpe ................ A61K 39/395 424/155.1 |
| 2006/0094659 | A1 | 5/2006 | Kew et al. |
| 2006/0127902 | A1 | 6/2006 | Madden et al. |
| 2007/0154897 | A1 | 7/2007 | Yen et al. |

FOREIGN PATENT DOCUMENTS

| KR | 1020050076876 | 7/2005 |
|---|---|---|
| WO | 03/071279 | 8/2003 |
| WO | 2006110581 | 10/2006 |

OTHER PUBLICATIONS

Sharma et al., Exp. Mol. Pathol., 2006, 81:136-145.*
Tian et al., Dig Dis Sci, 2008, 53:65-72, published online: May 11, 2007.*
International Search Report dated Aug. 2010.
Vishwanatha et al, "Enhanced Expression of Annexin II in Human Pancreatic Carcinoma Cells and Primary Pancreatic Cancers," Carcinogenesis, vol. 14, No. 12, Dec. 1, 1993, pp. 2575-2579.
Rosty et al, "Identification of Hepatocarcinoma-Intestine-Pancreas/ Pancreatitis-Associated Protein I as a Biomarker for Pancreatic Ductal Adenocarcinoma by Protein Biochip Technology," Cancer Research, American Association for Cancer Research, vol. 62, No. 2, Mar. 15, 2002, pp. 1868-1875.
Esposito et al, "Tenascin C and annexin II expression in the process of pancreatic carcinogenesis," The Journal of Pathology, vol. 208, No. 5, Apr. 1, 2006, pp. 673-685.
Kumble et al, "Enhanced levels of annexins in pancreatic carcinoma cells of Syrian hamsters and their intrapancreatic allografts," Cancer Research, vol. 52, No. 1, Jan. 1, 1992, pp. 163-167.
Lutz et al, "A Lethally Irradiated Allogeneic Granulocyte-Macrophage Colony Stimulating Factor-Secreting Tumor Vaccine for Pancreatic Adenocarcinoma," Annals of Surgery, vol. 253, No. 2, Feb. 1, 2011, pp. 328-335.

(Continued)

*Primary Examiner* — Hong Sang
(74) *Attorney, Agent, or Firm* — Mintz Levin Cohn Ferris Glovsky and Popeo, P.C.; Peter F. Corless

(57) ABSTRACT

AnnexinA2 (ANXA2), a member of the Annexin family of calcium-dependent, phospholipid binding proteins, is one of a panel of identified antigens recognized by the post-vaccination sera of patients who demonstrated prolonged disease-free survival following multiple vaccinations. AnnexinA2 is abundantly expressed in pancreatic adenocarcinomas and cell surface/membrane AnnexinA2 increases with the progression from premalignant lesions to invasive pancreatic adenocarcinomas. The cytoplasmic to cell surface translocation of AnnexinA2 expression is critical for pancreatic cancer cell invasion. In addition, phosphorylation of AnnexinA2 at Tyrosine 23 is important for its localization to the cell surface and for the invasion of pancreatic cancer cells. Finally, loss of AnnexinA2 leads to the loss of the Epithelial-Mesenchymal Transition.

6 Claims, 12 Drawing Sheets

(56) References Cited

OTHER PUBLICATIONS

Supplementary European Search Report issued in related European Application No. 09831034, dated Jan. 15, 2013.
Chung et al., Mitogenesis, cell migration, and loss of focal adhesions induced by tenascin-C interacting with its cell surface receptor, annexin II. Molecular Biology of the Cell. Jun. 1, 1996;7(6):883-892).
Rescher et al., Tyrosine phosphorylation of annexin A2 regulates Rho-mediated actin rearrangement and cell adhesion. Journal of Cell Science. Jul. 1, 2008;121(13):2177-2185.
Shimamura et al., Clinicopathological Significance of Galectin-3 Expression in Ductal Adenocarcinoma of The Pancreas 1. Clin Cancer Res. Aug. 2002;8(8):2570-5.
Jhaveri et al., Using Quantitative Seroproteomics to Identify Antibody Biomarkers in Pancreatic Cancer. Cancer Immunol Res. Mar. 2016;4(3):225-33.
Coppin et al., CA-125, but not galectin-3, complements CA 19-9 for discriminating ductal adenocarcinoma versus non-malignant pancreatic diseases. Pancreatology. Jan.-Feb. 2016;16(1):115-20.
Samuel et al. The molecular and cellular heterogeneity of pancreatic ductal adenocarcinoma. Nat Rev Gastroenterol Hepatol. Jan. 2012;9(2):77-87.
Supplemental European Search Report, dated Dec. 12, 2016 in corresponding European Application No. 16182042.8.

* cited by examiner

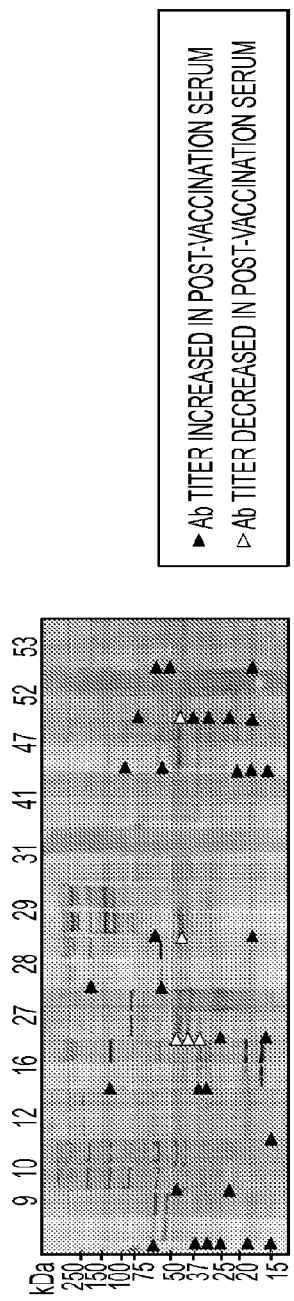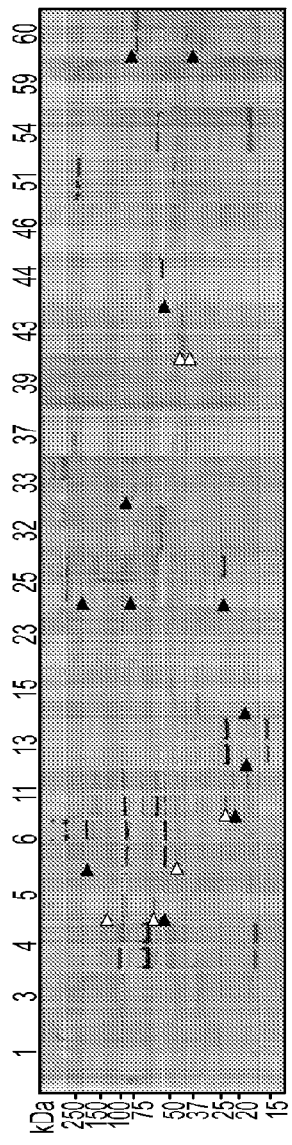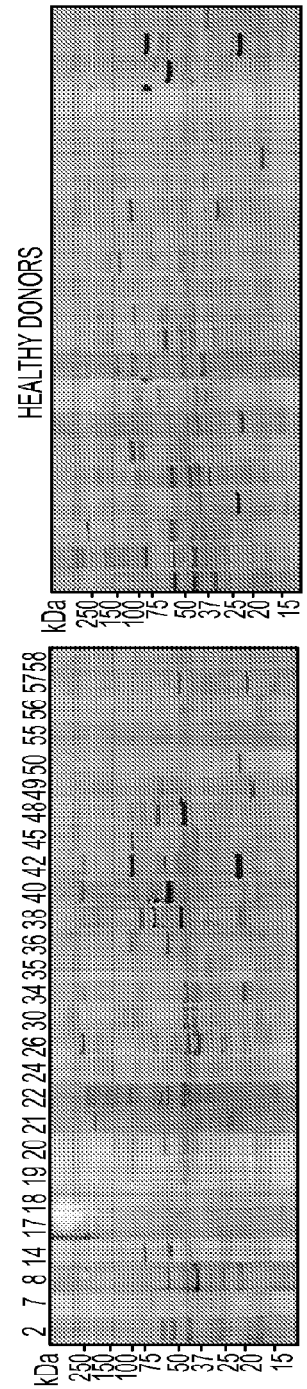

ANNEXIN A2 AS IMMUNOLOGICAL TARGET

This invention was made with government support under grant number CA062924 awarded by the National Institutes of Health. The government has certain rights in this invention.

TECHNICAL FIELD OF THE INVENTION

This invention is related to the area of tumor immunology. In particular, it relates to highly immunogenic proteins found on tumor cells.

BACKGROUND OF THE INVENTION

Pancreatic ductal adenocarcinoma (PDAC) is a devastating malignant disease with a median survival of less than 6 months and an overall 5-year survival rate of 1-4% (Pierantoni, Pagliacci et al. 2008). Lack of early diagnosis and effective systemic treatment are major reasons that account for these dismal survival rates. Morphologic and genetic analyses have implicated pancreatic intraepithelial neoplasm (PanIN) as a precursor lesion of human PDAC. PanINs appear to evolve in a stepwise manner through stages (PanIN1A, 1B, 2, 3) that display increasing cellular atypia and accumulate clonal mutations or aberrant expression of oncogenes or tumor suppressor genes such as K-Ras, p16, p53, and DPC4/SMAD4 in the course of progression to PDAC (Goggins, Kern et al. 1999). However, drugs that target these molecular abnormalities have not yet translated into improved clinical responses (Strimpakos, Saif et al. 2008). The aggressive nature of PDAC is featured by its early invasion and metastasis. This process in pancreatic cancer is also characterized by the epithelial-mesenchymal transition (Natalwala, Spychal et al. 2008). However, little is known about the molecular mechanisms underlying the early invasion and metastasis of PDAC. A better understanding of such mechanisms is believed to be essential for the identification of new targets for more effective treatments of PDAC. Thus, the identification of additional biologic pathways that contribute to the pathogenesis of PDAC will enhance our understanding of its biology and will facilitate the development of improved therapeutic interventions for the treatment of this deadly disease.

Cancer immunotherapy is an emerging approach for the treatment of pancreatic cancer. Early clinical studies are also providing critical human reagents for developing methods to identify new candidate proteins and biologic pathways. In particular, immunized lymphocytes and sera are being used to develop functional genomic and proteomic approaches for identifying those proteins that are relevant to the cancer. We have developed an allogeneic, GM-CSF secreting pancreatic cancer vaccine approach (Jaffee, Hruban et al. 2001). Phase I and II trials evaluating this vaccine in patients with resected PDAC have demonstrated both clinical and immunologic responses (Jaffee, Hruban et al. 2001; Laheru, Lutz et al. 2008) (Lutz et al. Manuscript submitted). This whole-cell vaccine based immunotherapy approach has provided critical lymphocyte reagents to develop a functional genomic approach for identifying novel pancreatic cancer antigens that are the targets of the immune response. As a result, we have reported the identification of mesothelin as a T cell target expressed by PDACs of patients treated with the pancreatic cancer vaccine who also developed other evidence of immune responses. (Thomas, Santarsiero et al. 2004). Mesothelin is a GPI linked cell surface glycoprotein expressed by the majority of PDACs and appears to be an adhesion molecule involved in tumor metastasis (Argani, Iacobuzio-Donahue et al. 2001). A number of therapeutic interventions targeting this molecule are currently in phase I testing (Hassan and Ho 2008)

Humoral immune response is an important and integrated part of the immune mechanisms by which a host defends itself against pathogen assault. Antibodies generated from vaccinations are a major factor that has protected generations of children from deadly infectious diseases. On the other hand, antibodies can also mediate pathogenesis in many autoimmune diseases in which the antibodies target cellular components of the host, i.e., auto-antigens, which under normal physiological conditions are tolerated by host immune system (1). As in autoimmune diseases, antigens in cancer come from within. Indeed, a common repertoire of autoantibodies was found to be shared by cancer and autoimmune disease patients (2). In addition, a majority of these autoantibodies are directed against intracellular components, which leads to the assumption that autoantigens in both cancer and autoimmune diseases emerge from damaged cells (3). Yet, autoantibodies can be detected at the very early pre-malignant stage of cancer development when there is no obvious cancer cell death or inflammation (4). It appears that aberrant gene expression, post-translational modification, and/or protein re-localization in cancer cells gives rise to antigens that are expressed either (a) to a greater extent than in normal cells or (b) as "altered" molecules absent in corresponding normal cells, or (c) in cell compartments where they are not supposed to be under normal conditions (ectopic expression), e.g., nuclear or cytoplasmic proteins appearing on the cell surface and non-secreted proteins being secreted to extracellular milieu. These molecules are collectively named tumor associated antigens (TAAs).

Early attempts by Old and co-workers to analyze humoral responses to cancer cell surface antigens, used an autologous typing approach in which cultured tumor cells were tested for reactivity with serum samples from the same patient (5-9). The analysis of over 200 patients with melanoma, leukemia, malignant brain tumor and renal cancer revealed that sera from a majority of the patients reacted to both tumor and normal cells. In a few rare cases, serum reactivity was directed against antigens present only on autologous tumor cells (unique antigens) or shared on some allogeneic tumor cells (shared tumor antigens). The true nature of the unique or specific tumor antigens was not well defined. One shared antigen Old and co-workers discovered, gangliosides, was investigated further. All ganglioside-reactive antibodies detected in cancer patients were of the IgM class; this was also the immunoglobulin class induced by vaccination of melanoma patients with pure or modified gangliosides (10, 11), which means that no memory response was developed. Nonetheless, ganglioside GM2 antibody production in melanoma patients was associated with a prolonged disease-free interval and survival (12). With the advent of new assay methodologies, such as serological identification of antigens by recombinant expression cloning (SEREX), serological proteome analysis (SERPA) and protein microarrays, a large number of antibody-reactive tumor associated antigens (TAAs) were identified. For example, over 2700 sequences were identified by SEREX alone and have been deposited in the Cancer Immunome Database (13). However, the clinical significance of these TAAs and their antibodies largely remains unclear. Spontaneous antibodies against several TAAs such as p53, NY-ESO-1, and survivin were found more frequently in high-grade tumors and appeared to be associated with disease relapse and poor survival (14-17). High titers of Her2/neu and MUC1 antibodies could be detected at early stages and appeared to be markers of a favorable prognosis (18-20). On the other hand, regardless of whether the respective spontaneous antibodies predict poor or favorable prognosis, vaccination with NY-ESO-1 or MUC1 has been shown to readily induce both humoral and T cell responses that are beneficial to patients (21-23).

The majority of the TAAs identified thus far have been in melanoma and a few other cancers. For cancers like pancreatic cancer, in which TAAs are poorly characterized, whole tumor cell vaccines present a good source for investigating TAAs immunotherapy. Vaccination with irradiated whole tumor cells expressing granulocyte-macrophage colony-stimulating factor (GM-CSF) can induce potent systemic immune responses that are capable of eradicating tumors (24). GM-CSF-secreting tumor vaccines can induce both CD4$^+$ and CD8$^+$ T cell-mediated antitumor responses and a broad range of antibody responses (25-27). Recently, we completed a phase II trial on an allogeneic GM-CSF-secreting pancreatic tumor vaccine in 60 patients with stage 1, 2, and 3-resected pancreatic ductal adenocarcinoma (PDA) (28). Twelve of the 60 vaccinated patients have survived greater than 3 years and shown a favorable clinical response.

There is a continuing need in the art to identify targets that are physiologically relevant to the immune system of human cancer patients.

SUMMARY OF THE INVENTION

According to one embodiment of the invention a pharmaceutical composition comprising monoclonal antibodies is provided. The antibodies specifically bind to AnnexinA2.

An aspect of the invention is a method for treating a patient with a tumor to diminish risk of tumor invasion and/or metastatic progression. Monoclonal antibodies which specifically bind to AnnexinA2 are administered to the patient.

Another aspect of the invention is a method of treating a patient with a tumor to diminish risk of tumor invasion and/or metastatic progression. ANXA2 protein or a nucleic acid encoding ANXA2 to the patient is administered to the patient. A T cell or B cell response to ANXA2 is thereby induced.

Still another aspect of the invention is a method of screening for candidate drugs which inhibit tumor invasion and/or metastasis. One or more test substances are contacted with pancreatic cancer cells in culture. Subcellular localization of ANXA2 after the contacting is determined. One or more test substances are identified as candidate drugs for inhibiting tumor invasion and/or metastasis if the one or more test substances inhibit translocation of ANXA2 to the cell surface.

According to another aspect of the invention a method of screening for candidate drugs which inhibit tumor invasion and/or metastasis is provided. One or more test substances is contacted with pancreatic cancer cells in culture. Phosphorylation status of Tyr23 of ANXA2 is determined. One or more test substances are identified as candidate drugs for inhibiting tumor invasion and/or metastasis if the one or more test substances inhibit phosphorylation of Tyr23 of ANXA2.

Yet another aspect of the invention is a method of screening for candidate drugs which inhibit tumor invasion and/or metastasis. One or more test substances is contacted with cancer cells in an animal model of pancreatic cancer. Subcellular localization of ANXA2 after the contacting is determined. The one or more test substances is identified as a candidate drug for inhibiting tumor invasion and/or metastasis if the one or more test substances inhibit translocation of ANXA2 to the cell surface.

A further aspect of the invention is a method of screening for candidate drugs which inhibit tumor invasion and/or metastasis. One or more test substances is contacted with cancer cells in an animal model of pancreatic cancer. Phosphorylation status of Tyr23 of ANXA2 is determined. The one or more test substances are identified as candidate drugs for inhibiting tumor invasion and/or metastasis if the one or more test substances inhibit phosphorylation of Tyr23 of ANXA2.

Another embodiment of the invention is a vaccine for treating patients with a tumor which has been resected. The vaccine comprises ANXA2 or a nucleic acid encoding ANXA2.

These and other embodiments which will be apparent to those of skill in the art upon reading the specification provide the art with new tools for cancer treatment and anti-cancer drug discovery.

Total cell lysate from two vaccine tumor lines was resolved at 40 μg proteins/lane on 4-12% Bis-Tris SDS-PAGE and immunoblotted with 1:1,000 dilutions of serum samples from vaccinated patients 9, 12, 27, and 53 who survived greater than 5 years post-pancreaticoduodenectomy. Specific antibodies in the serum were detected with peroxidase-conjugated goat anti-human IgG. Date of serum sample collection is shown on top of each lane. Vaccination is indicated with an arrow.

FIGS. 2A-2D. Vaccine-Specific Antibody Response in all 60 Vaccinated Patients and 22 Healthy Donors.

Total cell lysate from two vaccine tumor lines was resolved at 40 μg proteins/lane on 4-12% Bis-Tris SDS-PAGE and immunoblotted with 1:1,000 dilutions of pre-vaccination (left lane) versus post-3$^{rd}$ vaccination (right lane) serum samples from each patient who completed at least 3 vaccinations. For patients who completed only the 1$^{st}$ vaccination and the healthy donors, only pre-vaccination (patients) or a single time point sera (donors) were tested. Specific antibodies in the serum were detected with peroxidase-conjugated goat anti-human IgG. (FIG. 2A) Patients with disease-free survival (DFS)>3 years (n=12); FIG. 2 (B) Patients with DFS<3 years (n=21); (FIG. 2C) Patients who completed only the first vaccination (n=27); and (FIG. 2D) Healthy donors (n=22). Filled arrow indicates an increased antibody titer in the post-vaccination sera and open arrow a decreased antibody titer.

Figure 3:
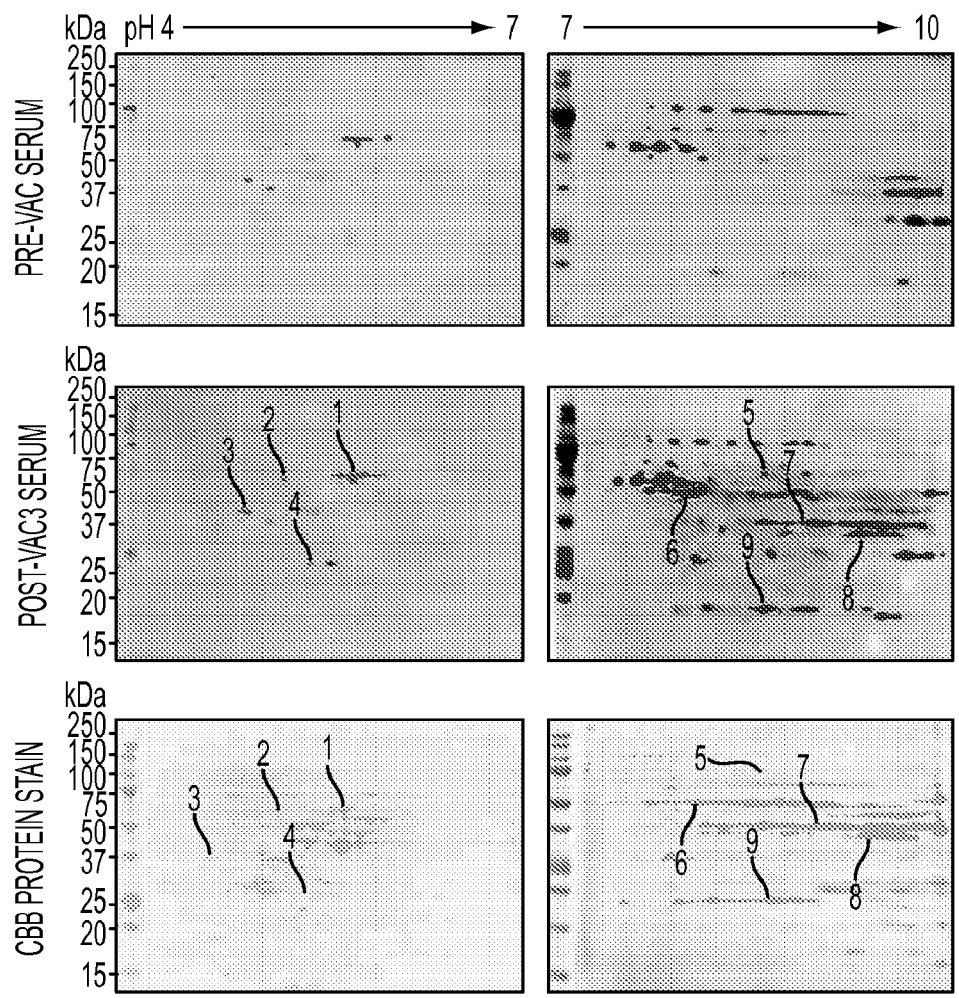

FIG. 3. Identification of Antibody-Reactive Proteins by Serological Proteomics.

Total cell lysate was pre-fractionated by microscale solution IEF on a ZOOM IEF Fractionator into 2 fractions. Each fraction was then subjected to 2-dimensional electrophoresis and immunoblotting with pre-v.s. post-vaccination serum samples. Protein spots on a Coomassie-stained gel, which corresponds to those detected preferentially by post-vaccination sera on immunoblotting, were excised and digested with trypsin. The generated peptides were analyzed by MALDI-TOF MS and the protein identity was obtained by searching Peptide Mass Fingerprint database NCBInr using the Mascot online search engine. Shown is a representative result with serum samples from patient 9 and the proteins identified by mass spectrometry.

Figure 4A:
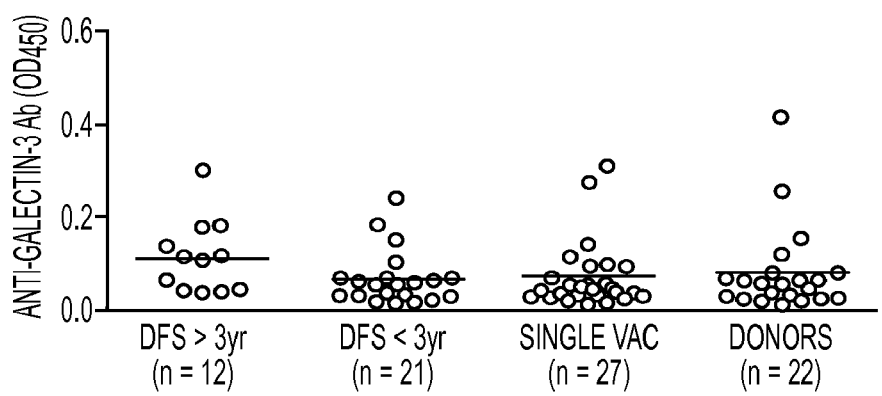
Figure 4B:
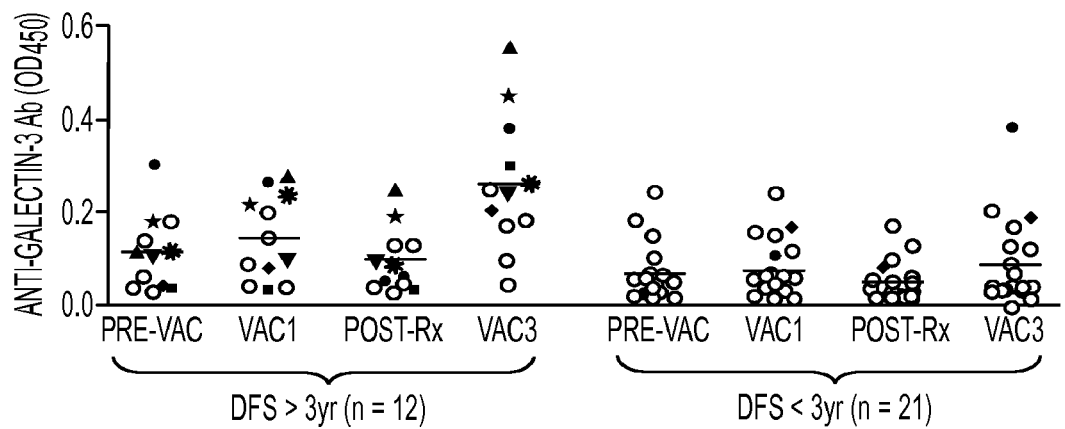
Figure 4C:
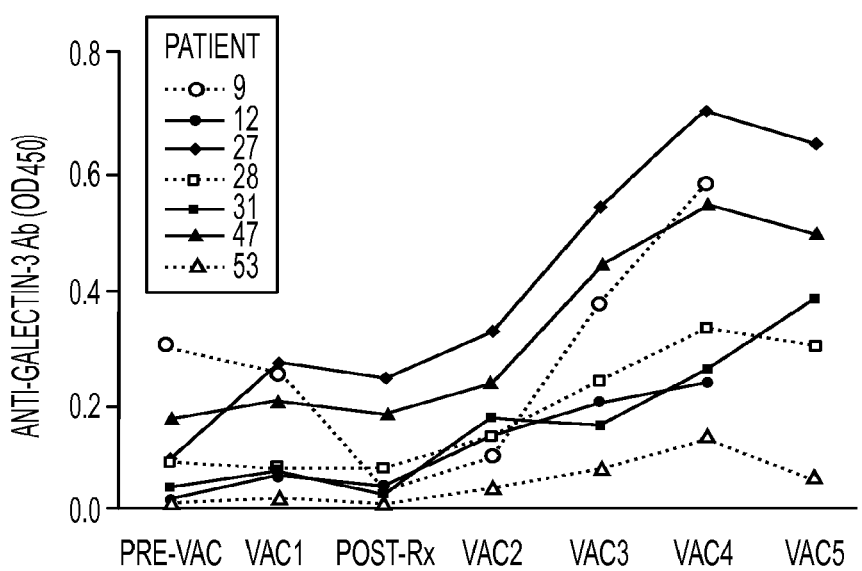

FIGS. 4A-4C. Vaccine-Induced Galectin-3 Antibody Response Correlated with Clinical Outcome.

Serum samples were tested by ELISA for antibody response against recombinant galectin-3. $OD_{450}$ values at a serum dilution of 1:400 are shown. (FIG. 4A) Pre-existing anti-galectin-3 antibody in pre-vaccination serum samples from vaccinated patients and serum samples from healthy donors. Each symbol represents a patient or donor. (FIG. 4B) The time course of anti-galectin-3 antibody titer changes in patients who completed at least 3 vaccinations. Antibody titers shown are at pre-vaccination (Pre-Vac), 14 days post-$1^{st}$ vaccination (Vac 1), 1 month post-radiochemotherapy (Post-Rx), and 1 month post-$3^{rd}$ vaccination (Vac 3). A solid symbol indicates an elevated antibody titer in the post-vaccination sera. (FIG. 4C) The detailed time course of anti-galectin-3 antibody titer changes at all time points in 7 patients who had an elevated antibody titer in their post-vaccination sera.

Figure 5A:
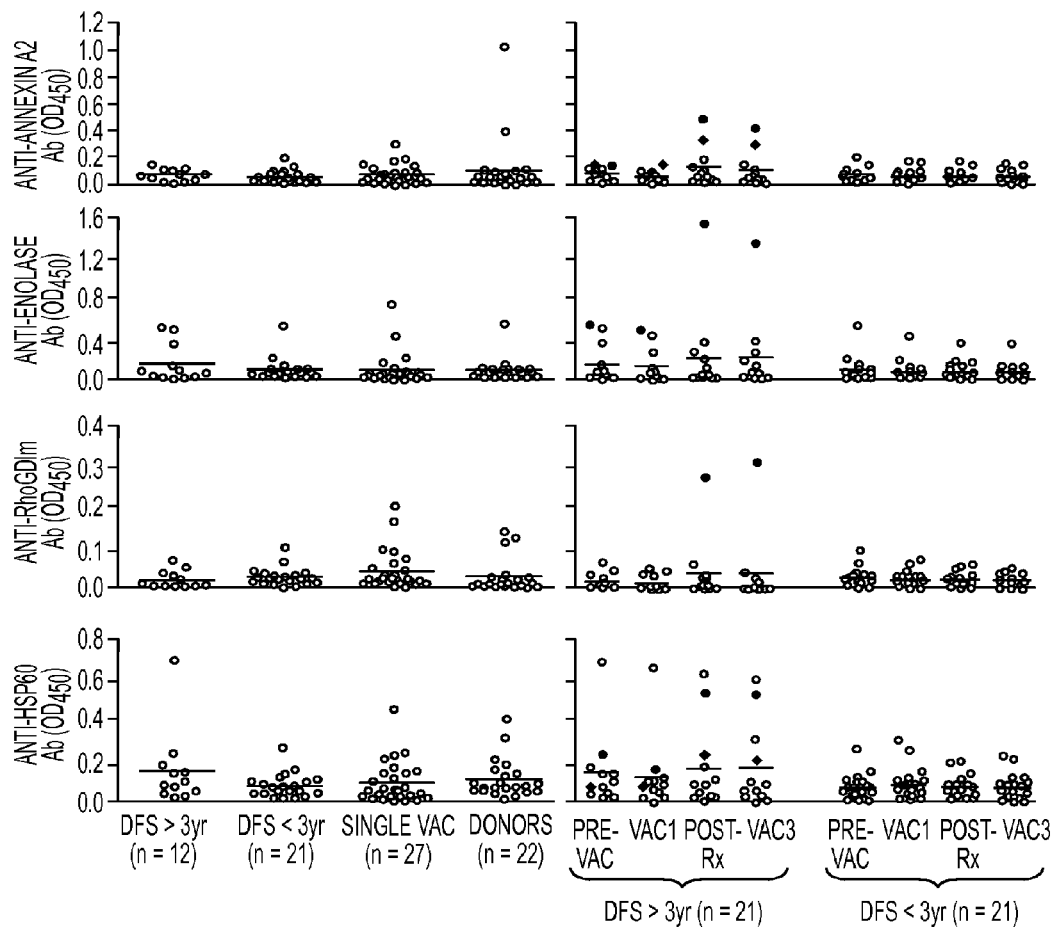
Figure 5B:
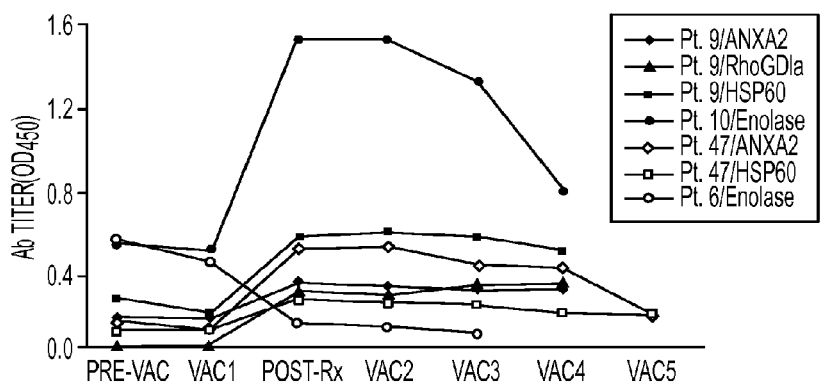

FIGS. 5A-5B. Antibody Response to AnnexinA2, Enolase, RhoGDIα or HSP60 was Enhanced by Radiation and Chemotherapy.

Serum samples were tested by ELISA for antibody response against recombinant proteins AnnexinA2, enolase, RhoGDI, or HSP60. $OD_{450}$ values at a serum dilution of 1:400 are shown. (FIG. 5A) Pre-existing antibody titer in pre-vaccination serum samples from vaccinated patients and serum samples from healthy donors (left panel) and the time course of antibody titer changes in patients who completed at least 3 vaccinations (right panel). Each symbol represents a patient or donor. Antibody titers shown are at pre-vaccination (Pre-Vac), 14 days post-$1^{st}$ vaccination (Vac 1), 1 month post-radiochemotherapy (Post-Rx), and 1 month post-$3^{rd}$ vaccination (Vac 3). A solid symbol indicates an elevated antibody titer in the post-vaccination sera. FIG. 5 (B) The detailed time course of antibody titer changes at all time points in patients 9, 10, and 47 who had an elevated antibody titer post-radiochemotherapy and patient 6 whose antibody titer to enolase declined over time.

Figure 6A:
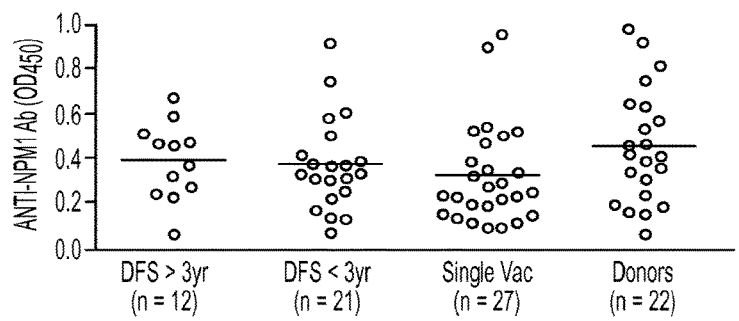
Figure 6B:
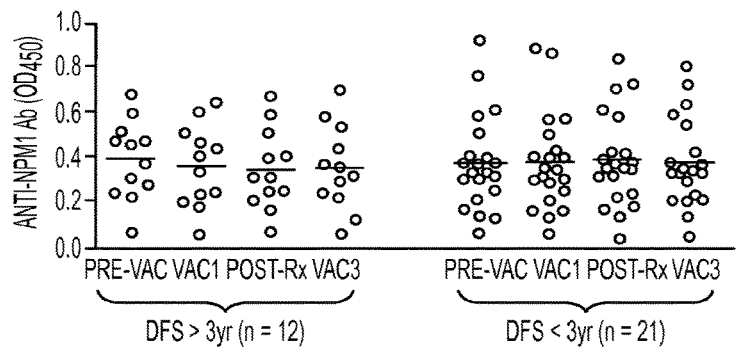
Figure 6C:
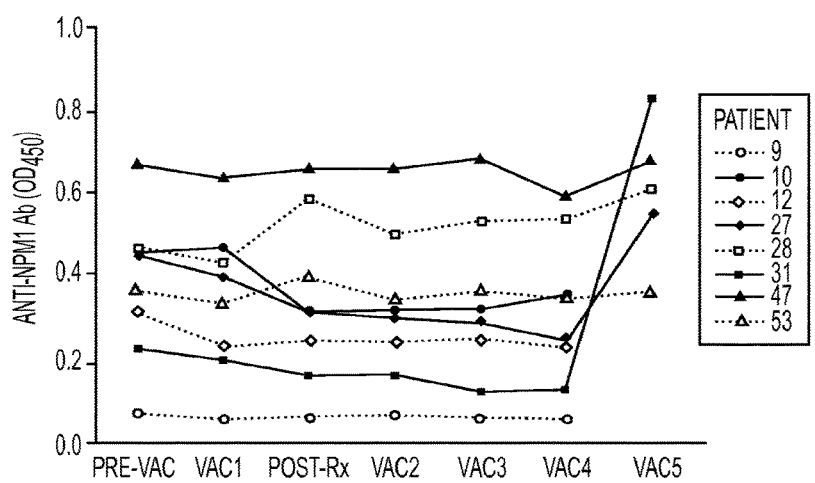

FIGS. 6A-6C. Intact Antibody Response to Influenza Proteins in Vaccinated Patients.

Serum samples were tested by ELISA for antibody response against recombinant influenza fusion protein NPM1. $OD_{450}$ values at a serum dilution of 1:400 are shown. FIG. 6 (A) Pre-existing anti-NPM1 antibody in pre-vaccination serum samples from vaccinated patients and serum samples from healthy donors. Each symbol represents a patient or donor. (FIG. 6B) The time course of anti-NPM1 antibody titer changes in patients who completed at least 3 vaccinations. Antibody titers shown are at pre-vaccination (Pre-Vac), 14 days post-$1^{st}$ vaccination (Vac 1), 1 month post-radiochemotherapy (Post-Rx), and 1 month post-$3^{nd}$ vaccination (Vac 3). (FIG. 6C) The detailed time course of anti-NPM1 antibody titer changes at all time points in 8 patients who had an elevated antibody titer to tumor-derived proteins in their post-vaccination sera.

FIG. 7A-7E.

Figure 7A:
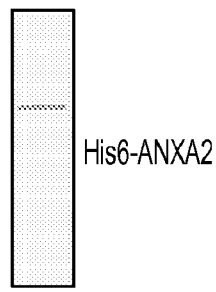
Figure 7B:
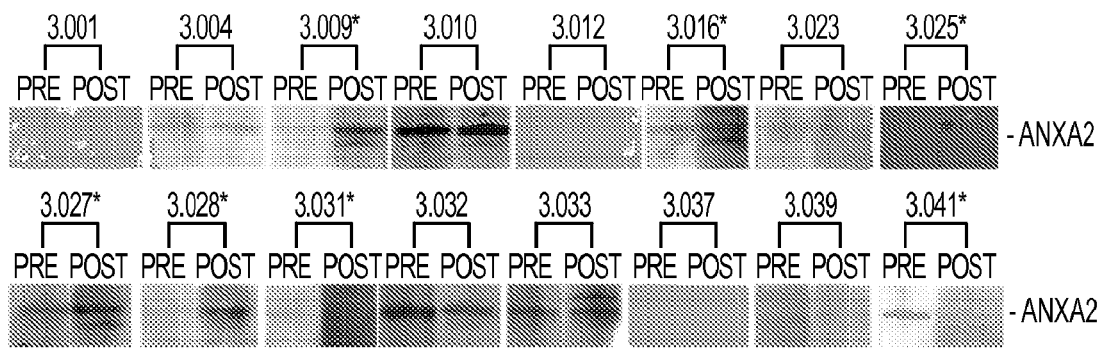
Figure 7C:
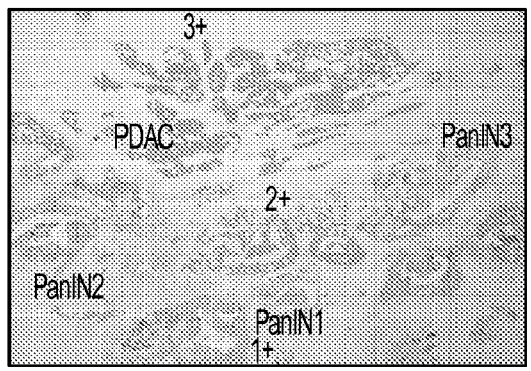
Figure 7D:
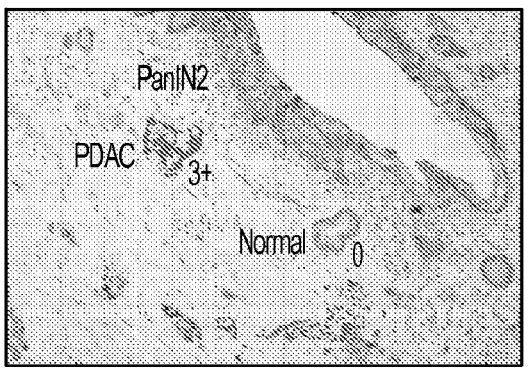
Figure 7E:
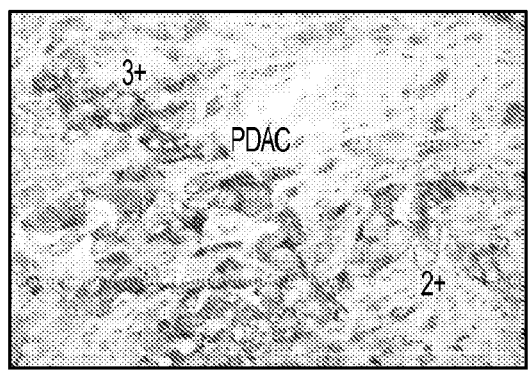

FIG. 7A shows purified recombinant His6-tagged AnnexinA2 (His6-ANXA2) on a SDS-PAGE gel stained with commassie blue. FIG. 7B. Purified His6 tagged AnnexinA2 (ANXA2) on a SDS-PAGE gel was western-blotted by pre- and post-vaccination serum. Patients marked by * had antibody induction, which was manifested by stronger signals of ANXA2 in western blot with post-vaccination serum vs. pre-vaccination serum. FIGS. 7C-7E, immunohistochemistry staining of AnnexinA2 in human pancreatic adenocarcinoma. AnnexinA2 expression with score 0, 1, 2, 3 was indicated. PanINs and PDAC were indicated.

FIGS. 8A-8C.

Figure 8A:
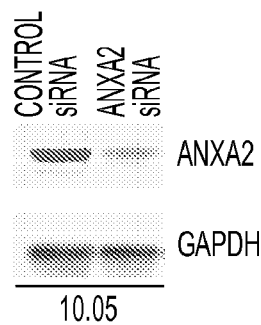
Figure 8B:
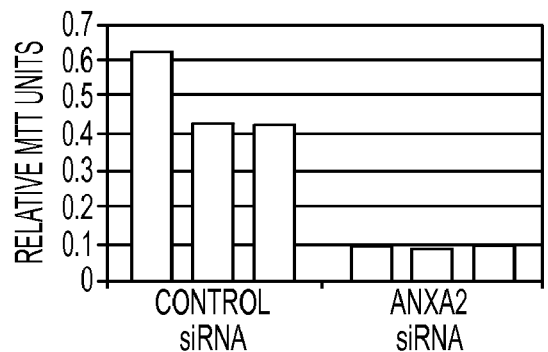
Figure 8C:
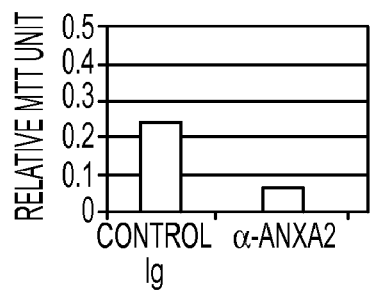

FIG. 8A. Western blot analysis showing that siRNA inhibits expression ANXA2. Whole cell extract from Panc10.05 treated with control siRNA and ANXA2 siRNA, respectively, was blotted by rabbit polyclonal anti-ANXA2 antibody (upper panel) and by rabbit polyclonal anti-GAPDH antibody (lower panel), respectively. FIG. 8B. In vitro invasion assay showing that ANXA2 siRNA inhibits the invasion capacity of the 10.05 pancreatic cancer cell line. Invaded cells were measured by MMT assays and normalized by total cell numbers. Triplicated experiments were done for control siRNA and ANXA2 siRNA, respectively. FIG. 8C. Anti-ANXA2 antibody inhibits invasion capacity of 10.05 cells. Rabbit polyclonal anti-ANXA2 antibody or control IgG was added into the culture media in a final concentration of 25 µg/ml throughout the in vitro invasion assays.

FIGS. 9A-9C.

Figure 9A:
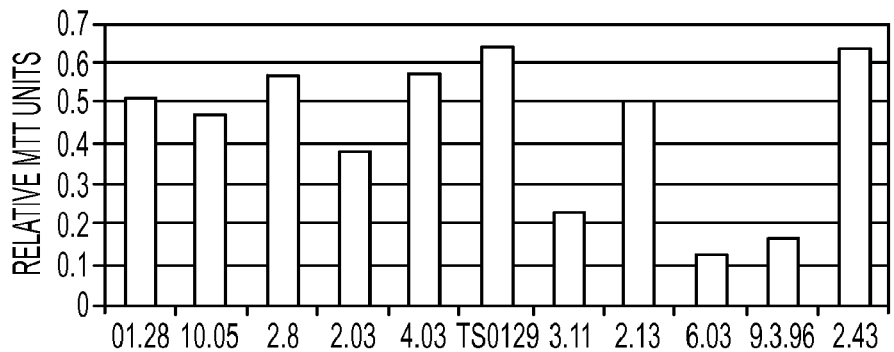
Figure 9B:
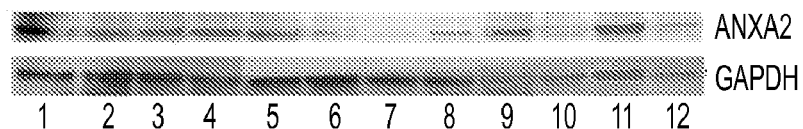
Figure 9C:
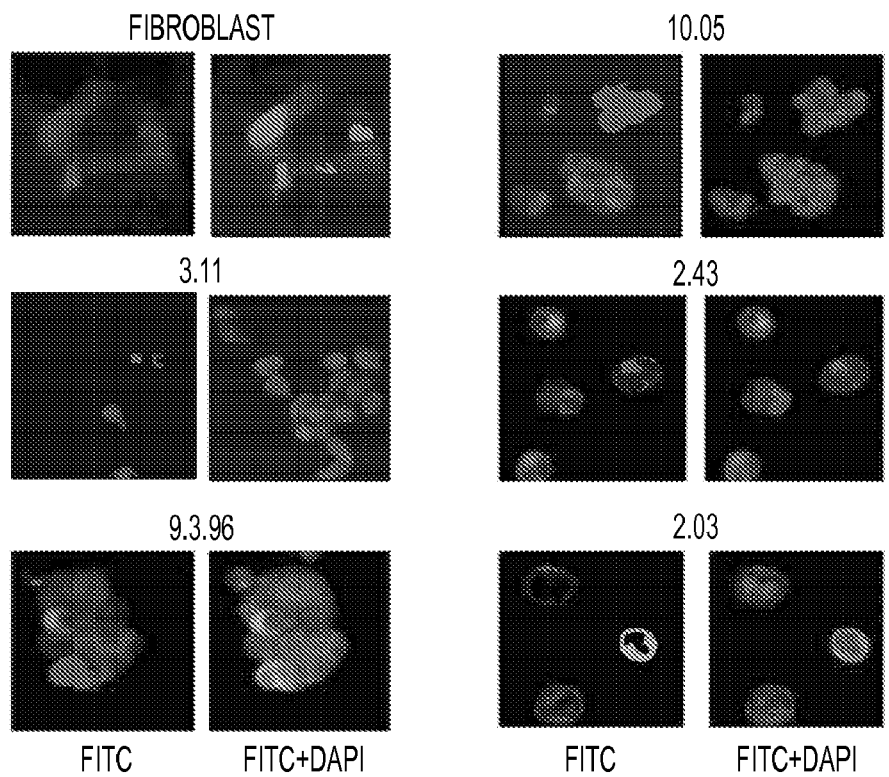

FIG. 9A. In vitro invasion of multiple pancreatic cancer cell lines. Invaded cells were measured by MTT assays. Shown are average MTT units on three parallel experiments after they were normalized by total cell numbers. FIG. 9B, expression of ANXA2 in each cell lines demonstrated by immunoblot analyses with anti-ANXA2 polyclonal antibody. Lanes 1-12 correspond to human pancreatic cancer cell lines: Panc01.28, Panc10.5, Panc2.8, Panc2.03, Panc4.03, PancTS0129, Panc3.11, Panc2.13, Panc6.03, Panc9.3.96, and Panc2.43, respectively; lane 13, human pancreatic para-cancerous fibroblast cells.) FIG. 9C, fluorescent immunostaining showed predominant cell surface localization of ANXA2 in representative cells with higher invasion capacity (Panc10.05, Panc2.43, Panc2.03), but not in cells with lower invasion capacity (human fibroblast, nuclear/cytoplasmic staining; Panc3.11, perinuclear staining; MiaPaca-2, cytoplasmic/nuclear staining). FITC indicates the images of immunostaining with rabbit anti-ANXA2 polyclonal antibody and FITC-conjugated secondary antibody. FITC+DAPI indicates the overlapped images of FITC staining of ANXA2 and DAPI staining of nuclei.

FIGS. 10A-10C.

Figure 10A:
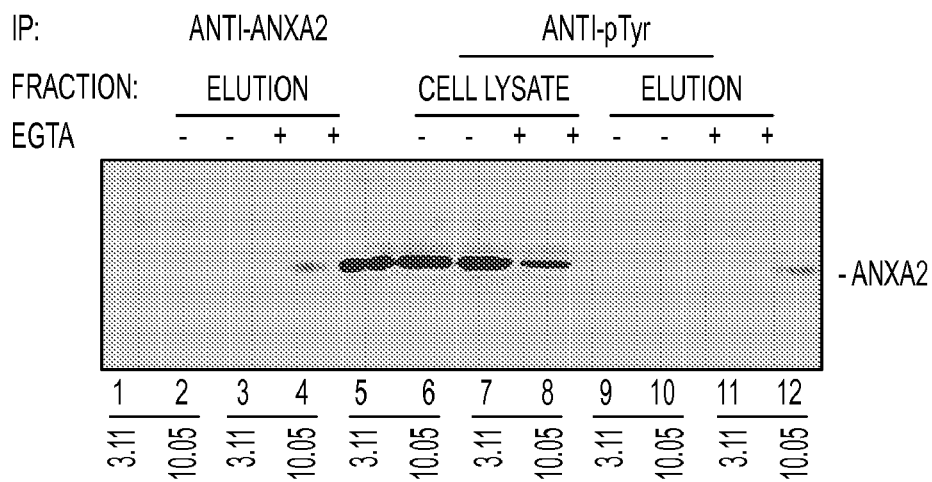
Figure 10B:
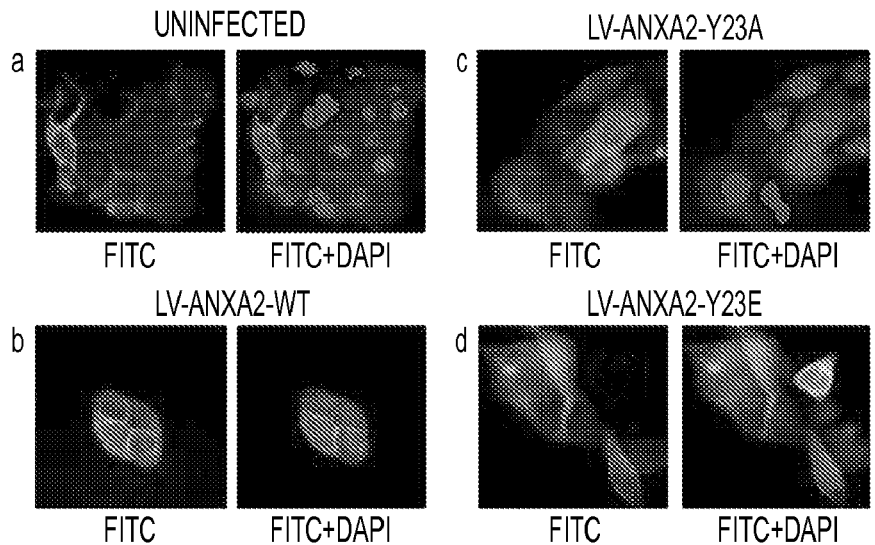
Figure 10C:
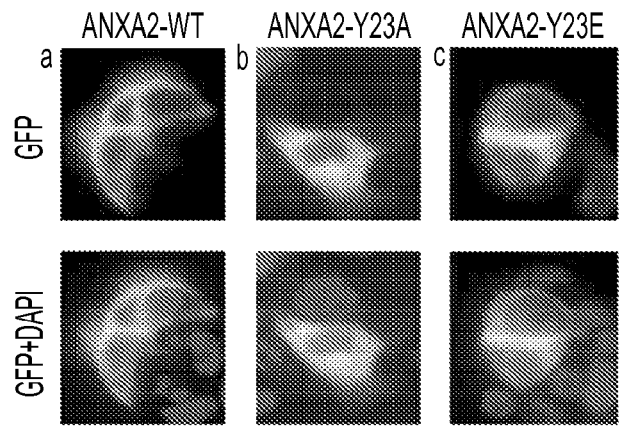

FIG. 10A. Panc10.05 and Panc3.11 cells were either incubated with the EGTA containing buffer or the EGTA-free buffer. The two different elutions from two different cell lines as indicated were immunoprecipitated by anti-ANXA2 antibodies (lanes 1-4) or anti-phosphotyrosine antibodies (lanes 9-12). After elution, the two cell lines were lysed and the lysates were immunoprecipitated by the anti-phosphotyrosine antibodies (anti-pTry) (lanes 5-8). FIG. 10 B. Fluorescent immunostaining of ANXA2 in cells either uninfected (panel a) or infected with lentivirus expressing wild-type ANXA2 (panel b), with lentivirus expressing Y23A mutated ANXA2 (panel c) or with lentivirus expressing Y23E mutated ANXA2 (panel d). FITC images or overlapped images of FITC and DAPI staining were shown as indicated. FIG. 10C, GFP-tagged ANXA2 in Panc10.05 cells. a, GFP-tagged wild-type ANXA2; b, GFP-tagged Y23A-mutated ANXA2; c, GFP-tagged Y23E-mutated ANXA2. Upper panels: GFP signals; lower panels: overlapped images of GFP signals and DAPI staining of nuclei.

FIGS. 11A-11B

Figure 11A:
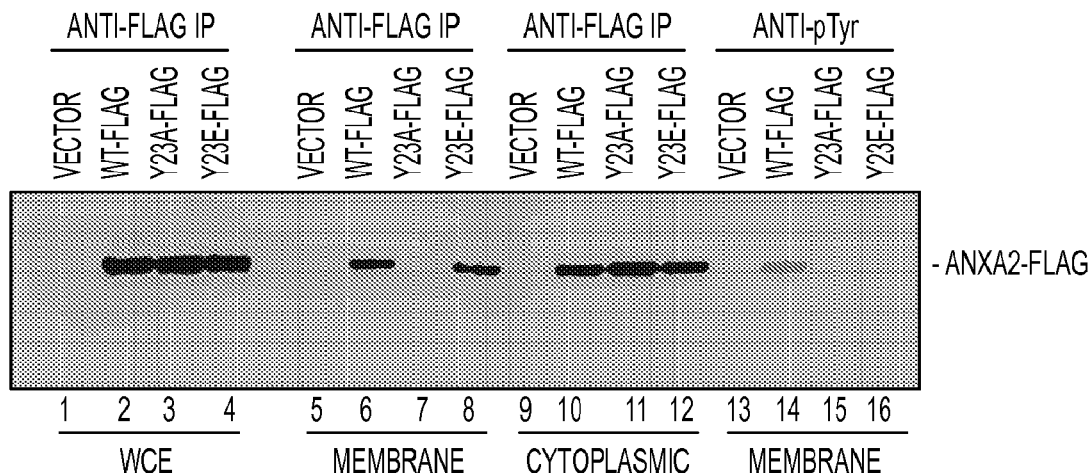
Figure 11B:
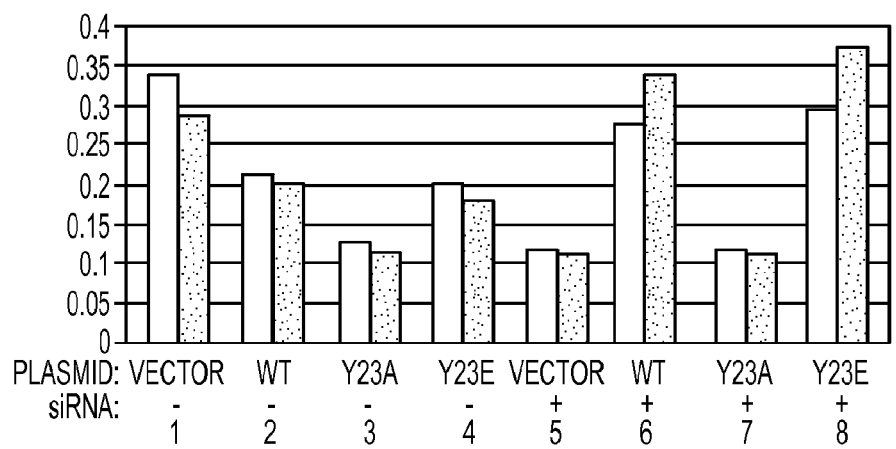

FIG. 11A. FLAG-tagged ANXA2 expression in Panc10.05 cells transfected by the pcDNA-based plasmid vector alone (lanes 1, 5, 9, 13), the plasmid carrying ANXA2$^{WT}$-FLAG (lanes 2, 6, 10, 14), the plasmid carrying ANXA2$^{Y23A}$-FLAG (lanes 3, 7, 11, 15), or the plasmid carrying ANXA2$^{Y23E}$-FLAG (lanes 4, 8, 12, 16). Whole cell extract (lanes 1-4), membrane fraction (lanes 5-8, 12-16), or cytoplasmic fraction (lanes 9-12) was obtained from these cells, respectively and immunoprecipated by either anti-FLAG M2 antibodies (lanes 1-12) or anti-phosphotyrosine antibodies (anti-pTry) (lanes 13-16). The immunoprecipitates were blotted by M2 antibodies. FIG. 11B. In vitro invasion of Panc10.05 cells transfected with the pcDNA-based plasmid vector alone (lanes 1, 5), the plasmid carrying ANXA2$^{WT}$-FLAG (lanes 2, 6), the plasmid carrying ANXA2$^{Y23A}$-FLAG (lanes 3, 7), or the plasmid carrying ANXA2$^{Y23E}$-FLAG (lanes 4, 8). Lanes 5-8 were also cotransfected with ANXA2 siRNA duplex. Results of duplicated experiments were show.

Figure 12:
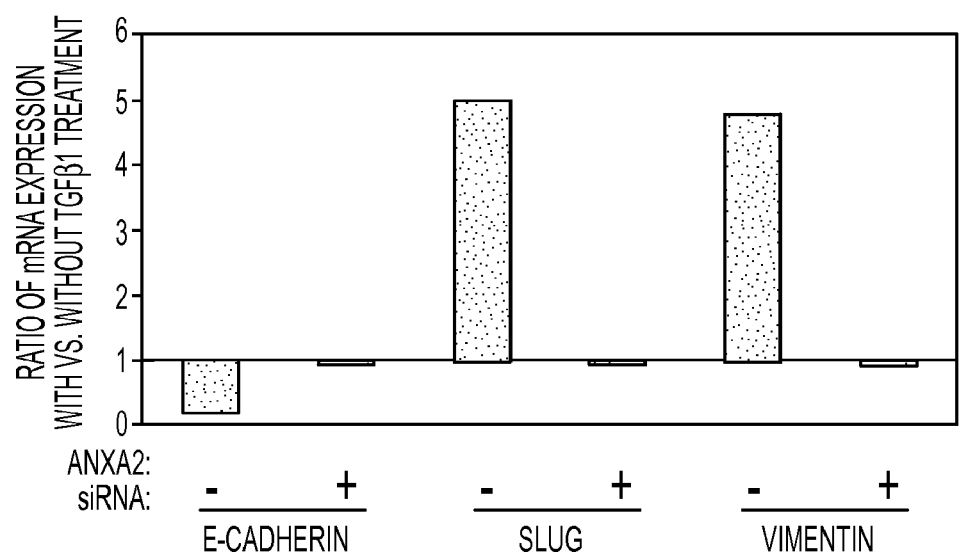

FIG. 12 Quantitative real-time PCR analyses of E-cadherin, slug, and vimentin mRNA expression in a pair of Panc10.05 cell lines, one with and the other without knockdown of ANXA2 by siRNA. The relative ratios of mRNA expression with TGFβ1 treatment vs. without TGF treatment are shown. The data were normalized with β-actin expression.

DETAILED DESCRIPTION OF THE INVENTION

The inventors have found that AnnexinA2 induces a strong immunological response in patients vaccinated with a whole cell tumor vaccine. Moreover, the inventors have found that in cancer cells, AnnexinA2 translocates to the cell surface and is phosphorylated on Tyrosine 23. Both the phosphorylation and the translocation are critical for tumor cell invasiveness and metastasis. An antibody response to AnnexinA2 in vaccinated patients correlates with a favorable clinical response, i.e., an improvement in length of disease-free survival. These results identify AnnexinA2 as an excellent immune target for inhibition of invasiveness and metastasis.

Immunological targeting of AnnexinA2 can be accomplished either passively, by administration of antibodies that specifically bind to AnnexinA2, or actively, by vaccination with peptide or nucleic acid vaccines. The peptide or nucleic acid vaccines comprise or encode, respectively, at least one T or B cell epitope of AnnexinA2. Antibodies according to the invention may be monoclonal or polyclonal. They may be human, mouse, rat, goat, horse, or chimeric. They may be humanized antibodies. Such generic types of antibodies and means of making them are well known in the art. Nucleic acids may be administered as part of vectors, for example viral or plasmid vectors. Naked DNA or protein-complexed DNA or polymer-complexed DNA, or viral encapsidated DNA may be used. Similarly RNA can be used with appropriate systems, such as RNA viruses. Protein vaccines may additionally comprise adjuvants.

Typically patients to be treated will already have had their primary tumors resected, treated with radiation, or treated with chemotherapy. However, there may be clinical situations where this is not the order of treatment. In some cases all of a tumor cannot be resected. In most cases it is impossible to know if all tumor tissue has been removed.

Tumors which are susceptible to AnnexinA2 targeting include without limitation pancreatic, prostate, liver, melanoma, and kidney. Other types which may be targeted include brain, colon, stomach, lung, breast, ovarian, hematologic, and esophageal cancers. Any tumor or cancer cell in which AnnexinA2 is found to be overexpressed is likely to be susceptible to such targeting.

The vaccines of the present invention can be administered by any means known in the art for inducing a T cell cytolytic response or a B cell humoral response. These means include oral administration, intravenous injection, percutaneous scarification, subcutaneous injection, intramuscular injection, and intranasal administration. The vaccines can be administered intradermally by gene gun. Gold particles coated with DNA may be used in the gene gun. Other inoculation routes as are known in the art can be used.

Additional agents which are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types aas macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Further additives, such as preservatives, stabilizers, adjuvants, antibiotics, and other substances can be used as well. Preservatives, such as thimerosal or 2-phenoxy ethanol, can be added to slow or stop the growth of bacteria or fungi resulting from inadvertent contamination, especially as might occur with vaccine vials intended for multiple uses or doses. Stabilizers, such as lactose or monosodium glutamate (MSG), can be added to stabilize the vaccine formulation against a variety of conditions, such as temperature variations or a freeze-drying process.

Viral vectors can be used to administer polynucleotides encoding a polypeptide comprising an AnnexinA2 epitope. Such viral vectors include vaccinia virus and avian viruses, such as Newcastle disease virus. Others may be used as are known in the art.

One particular method for administering polypeptide vaccine is by pulsing the polypeptide onto an APC or dendritic cell in vitro. The polypeptide binds to MHC molecules on the surface of the APC or dendritic cell. Prior treatment of the APCs or dendritic cells with interferon-γ can be used to increase the number of MHC molecules on the APCs or dendritic cells. The pulsed cells can then be administered as a carrier for the polypeptide. Peptide pulsing is taught in Melero et al., *Gene Therapy* 7:1167 (2000).

Naked DNA can be injected directly into the host to produce an immune response. Such naked DNA vaccines may be injected intramuscularly into human muscle tissue, or through transdermal or intradermal delivery of the vaccine DNA, typically using biolistic-mediate gene transfer (i.e., gene gun). Some reviews describing the gene gun and muscle injection delivery strategies for DNA immunization include Tuting, Curr. Opin. Mol. Ther. (1999) 1: 216-25, Robinson, Int. J. Mol. Med. (1999) 4: 549-55, and Mumper and Ledbur, Mol. Biotechnol. (2001) 19: 79-95. Other possible methods for delivering plasmid DNA includes electroporation and iontophoreses.

Another possible gene delivery system comprises ionic complexes formed between DNA and polycationic liposomes (see, e.g., Caplen et al. (1995) Nature Med. 1: 39). Held together by electrostatic interaction, these complexes may dissociate because of the charge screening effect of the polyelectrolytes in the biological fluid. A strongly basic lipid composition can stabilize the complex, but such lipids may be cytotoxic.

The use of intracellular and intercellular targeting strategies in DNA vaccines may further enhance the AnnexinA2-specific antitumor effect. Previously, intracellular targeting strategies and intercellular spreading strategies have been used to enhance MHC class I or MHC class II presentation of antigen, resulting in potent CD8+ or CD4+ T cell-mediated antitumor immunity, respectively. For example, MHC class I presentation of a model antigen, HPV-16 E7, was enhanced using linkage of *Mycobacterium tuberculosis* heat shock protein 70 (HSP70) (Chen, et al., (2000), Cancer Research, 60: 1035-1042), calreticulin (Cheng, et al., (2001) J Clin Invest, 108:669-678) or the translocation domain (domain II) of *Pseudomonas aeruginosa* exotoxin A (ETA (dII)) (Hung, et al., (2001) Cancer Research, 61: 3698-3703) to E7 in the context of a DNA vaccine. To enhance MHC class II antigen processing, the sorting signals of the lysosome associated membrane protein (LAMP-1) have been linked to the E7 antigen, creating the Sig/E7/LAMP-1 chimera (Ji, et al, (1999), *Human Gene Therapy*, 10: 2727-2740). To enhance further the potency of naked DNA vaccines, an intercellular strategy that facilitates the spread of antigen between cells can be used. This improves the potency of DNA vaccines as has been shown using herpes simplex virus (HSV-1) VP22, an HSV-1 tegument protein that has demonstrated the remarkable property of intercellular transport and is capable of distributing protein to many surrounding cells (Elliot, et al., (1997) Cell, 88: 223-233). Such enhanced intercellular spreading of linked protein, results in enhancement of antigen-specific CD8+ T cell-mediated immune responses and antitumor effect. Any such methods can be used to enhance DNA vaccine potency against AnnexinA2-expressing tumors.

Polypeptides for immunization to raise a cytolytic T cell response are optionally from 8 to 25 amino acid residues in length. Any 8 contiguous amino acids of AnnexinA2 can be used as well. The polypeptides can be fused to other such epitopic polypeptides, or they can be fused to carriers, such as B-7, interleukin-2, or interferon-γ. The fusion polypeptide can be made by recombinant production or by chemical linkage, e.g., using heterobifunctional linking reagents. Mixtures of polypeptides can be used. These can be mixtures of epitopes for a single allelic type of an MHC molecule, or mixtures of epitopes for a variety of allelic types. The polypeptides can also contain a repeated series of an epitope sequence or different epitope sequences in a series.

Nucleic acids encoding AnnexinA2 may be used in any form, including as cDNA, genomic, full-length coding sequence, partial coding sequence, full-length transcript or copy of it, or short fragments encoding one or more epitopes. Sequence of AnnexinA2 nucleic acids are known in the art, and any can be used including NM_001002858.2, NM_001136015.2, NM_004039.2, and NM_001002857.1. Any of these or any which encode the protein products, such as NP_001002858.1 and NP 001002857.1 may be used.

Plasmids and viral vectors, for example, can be used to express a tumor antigen protein in a host cell. The host cell may be any prokaryotic or eukaryotic cell. Thus, for example, a nucleotide sequence derived from the cloning of AnnexinA2 proteins, encoding all or a selected portion of the full-length protein, can be used to produce a recombinant form of an AnnexinA2 polypeptide via microbial or eukaryotic cellular processes. The coding sequence can be ligated into a vector and the loaded vector can be used to transform or transfect hosts, either eukaryotic (e.g., yeast, avian, insect or mammalian) or prokaryotic (bacterial) cells. Such techniques involve standard procedures which are well known in the art.

Typically, expression vectors used for expressing a polypeptide, in vivo or in vitro contain a nucleic acid encoding an antigen polypeptide, operably linked to at least one transcriptional regulatory sequence. Regulatory sequences are art-recognized and can be selected to direct expression of the subject proteins in the desired fashion (time and/or place). Transcriptional regulatory sequences are described, for example, in Goeddel, Gene Expression Technology: Methods in Enzymology 185, Academic Press, San Diego, Calif. (1990).

Suitable vectors for the expression of a polypeptide comprising HLA-binding epitopes include plasmids of the types: pBR322-derived plasmids, pEMBL-derived plasmids, pEX-derived plasmids, pBTac-derived plasmids and pUC-derived plasmids for expression in prokaryotic cells, such as *E. coli*. Mammalian expression vectors may contain both prokaryotic and eukaryotic sequences in order to facilitate the propagation of the vector in bacteria, and one or more eukaryotic transcription units that can be expressed in eukaryotic cells. The pcDNAI/amp, peDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. Vaccinia and avian virus vectors can also be used. The methods which may be employed in the preparation of vectors and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

Other types of expression cassettes can also be used. For instance, the references described below in regard to viral, bacterial, and yeast vectors illustrate additional expression vectors which may be used in the present invention.

In another embodiment of the invention, a polypeptide described herein, or a polynucleotide encoding the polypeptide, is delivered to a host organism in an immunogenic composition comprising yeast. The use of live yeast DNA vaccine vectors for antigen delivery has been reviewed and reported to be efficacious in a mouse model using whole recombinant *Saccharomyces cerevisiae* yeast expressing tumor or HIV-1 antigens (see Stubbs et al. (2001) Nature Medicine 7: 625-29).

The use of live yeast vaccine vectors is known in the art. Furthermore, U.S. Pat. No. 5,830,463, the contents of which are incorporated herein by reference, describes particularly useful vectors and systems which can be used with the instant invention. The use of yeast delivery systems may be particularly effective for use in the tumor/cancer vaccine methods and formulations, as yeast appears to trigger cell-mediated immunity without the need for an additional adjuvant. Particularly preferred yeast vaccine delivery systems are nonpathogenic yeast carrying at least one recombinant expression system capable of modulating an immune response.

Bacteria can also be used as carriers for the epitopes of the present invention. Typically the bacteria used are mutant or recombinant. The bacterium is optionally attenuated. For instance, a number of bacterial species have been developed for use as vaccines and can be used in the present invention, including, but not limited to, *Shigella flexneri, E. coli, Listeria monocytogenes, Yersinia enterocolitica, Salmonella typhimurium, Salmonella typhi* or mycobacterium. The bacterial vector used in the immunogenic composition may be a facultative, intracellular bacterial vector. The bacterium may be used to deliver a polypeptide described herein to antigen-presenting cells in the host organism. The use of live bacterial vaccine vectors for antigen delivery has been reviewed (Medina and Guzman (2001) Vaccine 19: 1573-1580; Weiss and Krusch, (2001) Biol. Chem. 382: 533-41; and Darji et al. (2000) FEMS Immunol and Medical Microbiology 27: 341-9). Furthermore, U.S. Pat. Nos. 6,261,568 and 6,488,926, the contents of which are incorporated herein by reference, describe systems useful for cancer vaccines.

Bacterially mediated gene transfer is particularly useful in genetic vaccination by intramuscular, intradermal, or oral administration of plasmids; such vaccination leads to antigen expression in the vaccinee. Furthermore, bacteria can provide adjuvant effects and the ability to target inductive sites of the immune system. Furthermore, bacterial vaccine vectors have almost unlimited coding capacity. The use of bacterial carriers is often associated with still other significant benefits, such as the possibility of direct mucosal or oral delivery. Other direct mucosal delivery systems (besides live viral or bacterial vaccine carriers) which can be used include mucosal adjuvants, viral particles, ISCOMs, liposomes, and microparticles.

Both attenuated and commensal microorganisms have been successfully used as carriers for vaccine antigens. Attenuated mucosal pathogens which may be used in the invention include: *L. monocytogenes, Salmonella* spp., *V. cholorae, Shigella* spp., mycobacterium, *Y. enterocolitica*, and *B. anthracia*. Commensal strains which can be used in the invention include: *S. gordonii, Lactobacillus* spp., and *Staphylococcus* spp. The genetic background of the carrier strain used in the formulation, the type of mutation selected to achieve attenuation, and the intrinsic properties of the immunogen can be adjusted to optimize the extent and quality of the immune response elicited. The general factors to be considered to optimize the immune response stimulated by the bacterial carrier include: selection of the carrier; the specific background strain, the attenuating mutation and the level of attenuation; the stabilization of the attenuated phenotype and the establishment of the optimal dosage. Other antigen-related factors to consider include: intrinsic properties of the antigen; the expression system, antigen-display form and stabilization of the recombinant phenotype; co-expression of modulating molecules and vaccination schedules.

*Salmonella typhimurium* can be used as a bacterial vector in the immunogenic compositions of the invention. Use of this bacterium as an effective vector for a vaccine has been demonstrated in the art. For instance, the use of *S. typhimurium* as an attenuated vector for oral somatic transgene vaccination has been described (see Darji et al. (1997) Cell 91: 765-775; and Darji et al. (2000) FEMS Immun and Medical Microbiology 27: 341-9). Indeed most knowledge of bacteria-mediated gene transfer has been acquired using attenuated *S. typhimurium* as carrier. Two metabolically attenuated strains that have been used include *S. typhimurium* aroA, which is unable to synthesize aromatic amino acids, and *S. typhimurium* 22-11, which is defective in purine metabolism. Several antigens have been expressed using these carriers: originally, listeriolysin and actA (two virulence factors of *L. monocytogenes*) and beta-galactosidase (β-gal) of *E. coli* were successfully tested. Cytotoxic and helper T cells as well as specific antibodies could be detected against these antigens following oral application of a single dose of the recombinant *salmonella*. In addition, immunization with *Salmonella* carrying a listeriolysin-encoding expression plasmid elicited a protective response against a lethal challenge with *L. monocytogenes*. Oral transgene vaccination methodology has now been extended to include protective responses in herpes simplex virus 2 and hepatitis B infection models, with cell-mediated immune responses detected at the mucosal level.

In tumor models using β-gal as a surrogate tumor antigen, partial protective immunity against an aggressive fibrosarcoma was induced by orally administering *Salmonella* carrying a β-gal-encoding plasmid (see Paglia et al. (1998) Blood 92: 3172-76). In similar experiments using a β-gal-expressing transfectant of the murine renal cell carcinoma line RENCA, Zöller and Christ (Woo et al. (2001) Vaccine 19: 2945-2954) demonstrated superior efficacy when the antigen-encoding plasmid was delivered in bacterial carriers as opposed to using naked DNA. Interestingly, *Salmonella* can be used to induce a tumor growth retarding response against the murine melanoma B16; the *Salmonella* carry minigenes encoding epitopes of the autologous tumor antigens gp100 and TRP2 fused to ubiquitin. This suggests that under such circumstances peripheral tolerance towards autologous antigens can be overcome. This was confirmed by the same group (Lode et al. (2000) Med Ped Oncol 35: 641-646) using similar constructs of epitopes of tyrosine hydroxylase as autologous antigen in a murine neuroblastoma system. Furthermore, these findings were recently extended by immunizing mice that were transgenic for human carcinogenic antigen (hCEA) using a plasmid encoding a membrane-bound form of complete hCEA. In this case, a hCEA-expressing colon carcinoma system was tested and protection against a lethal challenge with the tumor could be improved by systemic application of interleukin 2 (IL-2) as adjuvant during the effector phase (see Xiang et al. (2001) Clin Cancer Res 7: 856s-864s).

Another bacterial vector which may be used in the immunogenic compositions described herein is *Salmonella typhi*. The *S. typhi* strain commonly used for immunization—Ty21a galE—lacks an essential component for cell-wall synthesis. Recently developed improved strains include those attenuated by a mutation in guaBA, which encodes an essential enzyme of the guanine biosynthesis pathway (Pasetti et al., Infect. Immun. (2002) 70:4009-18; Wang et al., Infect. Immun. (2001) 69:4734-41; Pasetti et al., Clin. Immunol. (1999) 92:76-89). Additional references describing the use of *Salmonella typhi* and/or other *Salmonella* strains as delivery vectors for DNA vaccines include the following: Lundin, Infect. Immun. (2002) 70:5622-7; Devico et al., Vaccine, (2002) 20:1968-74; Weiss et al., Biol. Chem. (2001) 382:533-41; and Bumann et al., FEMS Immunol. Med. Microbiol. (2000) 27:357-64.

The vaccines and immunogenic compositions of the present invention can employ *Shigella flexneri* as a delivery vehicle. *S. flexneri* represents the prototype of a bacterial DNA transfer vehicle as it escapes from the vacuole into the cytosol of the host cell. Several attenuated mutants of *S. flexneri* have been used successfully to transfer DNA to cell lines in vitro. Auxotrophic strains were defective in cell-wall synthesis (Sizemore et al. (1995) Science 270: 299-302 and Courvalin et al. (1995) C R Acad Sci Ser III, 318: 1207-12), synthesis of aromatic amino acids (Powell et al. (1996) Vaccines 96: Molecular Approaches to the Control of Infectious Disease; Cold Spring Harbor Laboratory Press) or synthesis of guanine nucleotides (Anderson et al. (2000) Vaccine 18: 2193-2202).

The vaccines and immunogenic compositions of the present invention may comprise *Listeria monocytogenes* (Portnoy et al, Journal of Cell Biology, 158:409-414 (2002); Glomski et al., Journal of Cell Biology, 156:1029-1038 (2002)). The ability of *L. monocytogenes* to serve as a vaccine vector has been reviewed in Wesikirch, et al., Immunol. Rev. 158:159-169 (1997). Strains of *Listeria monocytogenes* have recently been developed as effective intracellular delivery vehicles of heterologous proteins providing delivery of antigens to the immune system to induce an immune response to clinical conditions that do not permit injection of the disease-causing agent, such as cancer (U.S. Pat. No. 6,051,237; Gunn et al., J. of Immunology, 167: 6471-6479 (2001); Liau, et al., Cancer Research, 62: 2287-2293 (2002); U.S. Pat. No. 6,099,848; WO 99/25376; and WO 96/14087) and HIV (U.S. Pat. No. 5,830,702). A recombinant *L. monocytogenes* vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995)).

As a facultative intracellular bacterium, *L. monocytogenes* elicits both humoral and cell-mediated immune responses. Following entry of *Listeria* into a cell of the host organism, the *Listeria* produces *Listeria*-specific proteins that enable it to escape from the phagolysosome of the engulfing host cell into the cytosol of that cell. Here, *L. monocytogenes* proliferates, expressing proteins necessary for survival, but also expressing heterologous genes operably linked to *Listeria* promoters. Presentation of peptides of these heterologous proteins on the surface of the engulfing cell by MHC proteins permit the development of a T cell response. Two integration vectors that are useful for introducing heterologous genes into the bacteria for use as vaccines include pL1 and pL2 as described in Lauer et al., Journal of Bacteriology, 184: 4177-4186 (2002).

In addition, attenuated forms of *L. monocytogenes* useful in immunogenic compositions have been produced. The ActA protein of *L. monocytogenes* is sufficient to promote the actin recruitment and polymerization events responsible for intracellular movement. A human safety study has reported that oral administration of an actA/plcB-deleted attenuated form of *Listeria monocytogenes* caused no serious sequelae in adults (Angelakopoulos et al., Infection and Immunity, 70:3592-3601 (2002)). Other types of attenuated forms of *L. monocytogenes* have also been described (see, for example, WO 99/25376 and U.S. Pat. No. 6,099,848, which describe auxotrophic, attenuated strains of *Listeria* that express heterologous antigens).

*Yersinia enterocolitica* is another intraceullular bacteria that can optionally be used as a bacterial vector in immunogenic compositions of the present invention. The use of attenuated strains of *Yersini enterocolitica* as vaccine vectors is described in PCT Publication WO 02/077249.

In further embodiments of the invention, the immunogenic compositions of the invention comprise mycobacterium, such as *Bacillus* Calmette-Guerin (BCG). The *Bacillus* of Calmette and Guerin has been used as a vaccine vector in mouse models (Gicquel et al., Dev. Biol. Stand 82:171-8 (1994)). See also, Stover et al., Nature 351: 456-460 (1991).

Alternatively, viral vectors can be used. The viral vector will typically comprise a highly attenuated, non-replicative virus. Viral vectors include, but are not limited to, DNA viral vectors such as those based on adenoviruses, herpes simplex virus, avian viruses, such as Newcastle disease virus, poxviruses such as vaccinia virus, and parvoviruses, including adeno-associated virus; and RNA viral vectors, including, but not limited to, the retroviral vectors. Vaccinia vectors and methods useful in immunization protocols are described in U.S. Pat. No. 4,722,848. Retroviral vectors include murine leukemia virus, and lentiviruses such as human immunodeficiency virus. Naldini et al. (1996) Science 272: 263-267. Replication-defective retroviral vectors harboring a polynucleotide of the invention as part of the retroviral genome can be used. Such vectors have been described in detail. (Miller, et al. (1990) Mol. Cell. Biol. 10:4239; Kolberg, R. (1992) J. NIH Res. 4:43; Cornetta, et al. (1991) Hum. Gene Therapy 2:215).

Adenovirus and adeno-associated virus vectors useful in this invention may be produced according to methods already taught in the art. (See, e.g., Karlsson, et al. (1986) EMBO 5:2377; Carter (1992) Current Opinion in Biotechnology 3:533-539; Muzcyzka (1992) Current Top. Microbiol. Immunol. 158:97-129; Gene Targeting: A Practical Approach (1992) ed. A. L. Joyner, Oxford University Press, NY). Several different approaches are feasible.

Alpha virus vectors, such as Venezuelan Equine Encephalitis (VEE) virus, Semliki Forest virus (SFV) and Sindbis virus vectors, can be used for efficient gene delivery. Replication-deficient vectors are available. Such vectors can be administered through any of a variety of means known in the art, such as, for example, intranasally or intratumorally. See Lundstrom, Curr. Gene Ther. 2001 1:19-29.

Additional references describing viral vectors which could be used in the methods of the present invention include the following: Horwitz, M. S., Adenoviridae and Their Replication, in Fields, B., et al. (eds.) Virology, Vol. 2, Raven Press New York, pp. 1679-1721, 1990); Graham, F. et al., pp. 109-128 in Methods in Molecular Biology, Vol. 7: Gene Transfer and Expression Protocols, Murray, E. (ed.), Humana Press, Clifton, N.J. (1991); Miller, et al. (1995)

FASEB Journal 9:190-199, Schreier (1994) Pharmaceutica Acta Helvetiae 68:145-159; Schneider and French (1993) Circulation 88:1937-1942; Curiel, et al. (1992) Human Gene Therapy 3:147-154; WO 95/00655; WO 95/16772; WO 95/23867; WO 94/26914; WO 95/02697 (Jan. 26, 1995); and WO 95/25071.

In another form of vaccine, DNA is complexed with liposomes or ligands that often target cell surface receptors. The complex is useful in that it helps protect DNA from degradation and helps target plasmid to specific tissues. The complexes are typically injected intravenously or intramuscularly.

Polynucleotides used as vaccines can be used in a complex with a colloidal dispersion system. A colloidal system includes macromolecule complexes, nanocapsules, microspheres, beads, and lipid-based systems including oil-in-water emulsions, micelles, mixed micelles, and liposomes. One colloidal system that may be used with this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g., with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647.

In addition, complex coacervation is a process of spontaneous phase separation that occurs when two oppositely charged polyelectrolytes are mixed in an aqueous solution. The electrostatic interaction between the two species of macromolecules results in the separation of a coacervate (polymer-rich phase) from the supernatant (polymer-poor phase). This phenomenon can be used to form microspheres and encapsulate a variety of compounds. The encapsulation process can be performed entirely in aqueous solution and at low temperatures, and has a good chance, therefore, of preserving the bioactivity of the encapsulant. In developing an injectable controlled release system, the complex coacervation of gelatin and chondroitin sulfate to encapsulate a number of drugs and proteins has been exploited (see Truong, et al. (1995) Drug Delivery 2: 166) and cytokines have been encapsulated in these microspheres for cancer vaccination (see Golumbek et al. (1993) Cancer Res 53: 5841). Anti-inflammatory drugs have also been incorporated for intra-articular delivery to the joints for treating osteoarthritis (Brown et al. (1994) 331: 290). U.S. Pat. Nos. 6,193,970, 5,861,159 and 5,759,582, describe compositions and methods of use of complex coacervates for use as DNA vaccine delivery systems of the instant invention. In particular, U.S. Pat. No. 6,475,995, the contents of which are incorporated herein by reference, teaches DNA vaccine delivery systems utilizing nanoparticle coacervates of nucleic acids and polycations which serve as effective vaccines when administered orally.

To test candidate cancer vaccines in a mouse model, the candidate vaccine containing the desired tumor antigen can be administered to a population of mice either before or after challenge with a tumor cell line. Thus the mouse model can be used to test for both therapeutic and prophylactic effects. Vaccination with a candidate vaccine can be compared to control populations that are either not vaccinated, vaccinated with vehicle alone, or vaccinated with a vaccine that expresses an irrelevant antigen. If the vaccine is a recombinant microbe, its relative efficacy can be compared to a population of microbes in which the genome has not been modified to express the antigen. The effectiveness of candidate vaccine can be evaluated in terms of effect on tumor or ascites volume or in terms of survival rates. The tumor or ascites volume in mice vaccinated with candidate vaccine may be about 5%, about 10%, about 25%, about 50%, about 75%, about 90% or about 100% less than the tumor volume in mice that are either not vaccinated or are vaccinated with vehicle or a vaccine that expresses an irrelevant antigen. The differential in tumor or ascites volume may be observed at least about 10, at least about 17, or at least about 24 days following the implantation of the tumor cells into the mice. The median survival time in mice vaccinated with a nucleic acid-modified microbe may be, for example, at least about 2, at least about 5, at least about 7, or at least about 10 days longer than in mice that are either not vaccinated or are vaccinated with vehicle or a vaccine that expresses an irrelevant antigen.

The mouse model can be used to test any kind of cancer treatment known in the art. These may be conventional or complementary medicines. These can be immunological agents or cytotoxic agents. For example, the candidate cancer treatment may be radiation therapy, chemotherapy, or surgery. The candidate cancer treatment may be a combination of two or more therapies or prophylaxes, including but not limited to anti-cancer agents, anti-tumor vaccines, radiation therapy, chemotherapies, and surgery.

Any oncogene known in the art can be used to make the peritoneal or mesothelium cell line for making a mouse model. Such oncogenes include without limitation, Ki-ras, Erb-B2, N-ras, N-myc, L-myc, C-myc, ABL1, EGFR, Fos, Jun, c-Ha-ras, and SRC.

The vaccines, polynucleotides, polypeptides, cells, and viruses of the present invention can be administered to either human or other mammals. The other mammals can be domestic animals, such as goats, pigs, cows, horses, and sheep, or can be pets, such as dogs, rabbits, and cats. The other mammals can optionally be experimental subjects, such as mice, rats, rabbits, monkeys, or donkeys.

A reagent used in therapeutic methods of the invention is present in a pharmaceutical composition. Pharmaceutical compositions typically comprise a pharmaceutically acceptable carrier, which meets industry standards for sterility, isotonicity, stability, and non-pyrogenicity and which is nontoxic to the recipient at the dosages and concentrations employed. The particular carrier used depends on the type and concentration of the therapeutic agent in the composition and the intended route of administration. If desired, a stabilizing compound can be included. Formulation of pharmaceutical compositions is well known and is described, for example, in U.S. Pat. Nos. 5,580,561 and 5,891,725.

The determination of a therapeutically effective dose is well within the capability of those skilled in the art. A therapeutically effective dose refers to that amount of active ingredient that increases anti-tumor cytolytic T-cell activity relative to that which occurs in the absence of the therapeutically effective dose.

For any substance, the therapeutically effective dose can be estimated initially either in cell culture assays or in animal models, usually mice, rabbits, dogs, or pigs. The animal model also can be used to determine the appropriate concentration range and route of administration. Such information can then be used to determine useful closes and routes for administration in humans.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination (s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Effective in vivo dosages of polynucleotides and polypeptides are in the range of about 100 ng to about 200 ng, 500 ng to about 50 mg, about 1 µg to about 2 mg, about 5 µg to about 500 µg, and about 20 µg to about 100 µg.

Test substances which can be tested for use as a potential drug or immune enhancing agent can be any substance known in the art. The substance can be previously known for another purpose, or it can be previously unknown for any purpose. The substance can be a purified compound, such as a single protein, nucleic acid, or small molecule, or it can be a mixture, such as an extract from a natural source. The substance can be a natural product, or it can be a synthetic product. The substance can be specifically and purposefully synthesized for this purpose or it can be a substance in a library of compounds which can be screened.

We report below a study of antibody response in 60 pancreatic ductal adenocarcinoma (PDA) patients in a phase II trial of an allogeneic granulocyte-macrophage colony stimulating factor (GM-CSF)-secreting tumor cell vaccine. Our results showed that diverse antibody reactions to antigens derived from the tumor vaccine lines could be detected by Western blot analysis. Each patient appeared to have a distinct antibody response profile. In addition, elevated antibody titers to a variety of proteins were positively associated with patients' survival. Using a serological proteomics approach, we identified 14 proteins to which an elevated antibody activity was detected in the post-vaccination sera from 4 patients who survived greater than 5 years. Interestingly, two distinct types of antibody response were observed when chronological changes of antibody titer were tested by enzyme-linked immunosorbent assay (ELISA) with 5 purified recombinant proteins.

One type of antibody response was that against a galactoside-binding protein galectin-3. Eight out of 12 patients with Disease Free Survival (DFS)>3 years developed galectin-3-specific antibody response as compared with patients with DFS<3 years in which only 2 out of 21 patients did. This type of antibody response is characterized by a close relationship between antibody response development and vaccination, indicating that the antibody response was induced and/or augmented by the vaccine. The fact that galectin-3-specific antibody response in 4 patients was transiently suppressed by radiation and chemotherapy implies a recently developed response possibly by $1^{st}$ vaccination. This appears similar to Montero, et al.'s report of an animal study in which chemotherapy after vaccine priming induced transient B cell depletion followed by an expansion of antibody-forming cells specific for the priming antigen (35). Galectin-3 is a member of the β-galactoside-binding lectin (galectin) family which contains a conserved C-terminal carbohydrate-recognition-binding domain and a unique N-terminal proline- and glycine-rich domain (36). It is ubiquitously expressed in different types of cells and tissues and has multiple biological functions depending on its subcellular localization. Galectin-3 is mainly a cytoplasmic protein, but can easily translocate into the nucleus or be secreted to the extracellular milieu. It can also be found on the cell surface. Nuclear galectin-3 is involved in pre-mRNA processing, cell cycle regulation, and regulation of cancer-related gene expression (37). Cytoplasmic galectin-3 has anti-apoptotic activity by interacting with several apoptosis regulators such as Bcl-2, CD95, nucling, and Alix/AIP1. It also modulates several signaling pathways including K-Ras signaling. Extracellular galectin-3 mediates cell adhesion, migration, and cell-cell interactions (36). Expression of galectin-3 in a variety of tumors has been associated with high invasiveness, tumor progress, and metastasis (38-40). Recent evidence shows that galectin-3 is also a direct negative regulator of T cell activation by interfering TCR-CD8 colocalization in CD8 T cell activation (41) or down-regulating TCR and thus destabilizing immunological synapse in CD4 T cell activation (42). Small molecule inhibitors targeting galectin-3 have been shown to counteract its anti-apoptotic activity and enhance chemosensitivity and radio-sensitivity of cancer cells. When combined with chemotherapy, these inhibitors significantly reduce cancer metastasis and increase survival in an animal model (43, 44). The fact we observed in this study that galectin-3 antibody response was associated with a favorable clinical outcome could implicate a new line of cancer immunotherapeutic agent, i.e., anti-galectin-3 antibody. Whether anti-galectin-3 antibody acts as a neutralizer to reverse galectin-3's negative regulation of T cell activation or acts on its other cancer-related functions remains to be determined.

In contrast to galectin-3 antibody response, a second type of antibody response observed in this study was clearly enhanced by radiation and chemotherapy and appeared to be less associated with vaccinations. Although only a few patients showed this type of antibody response, they were all from the long disease-free survival group. Four of 5 proteins tested in this study, AnnexinA2, enolase α, HSP60, and RhoGDIα, were antigens for this type of antibody response. All 4 proteins have been reported to be overexpressed in pancreatic cancers (45-48) and actively involved in tumor angiogenesis, progression, invasion and metastasis (45, 49-56). These 4 proteins are, therefore, good targets for cancer therapy including immunotherapy. Antibody response to AnnexinA2, enolase α and RhoGDIα could be detected at the very early pre-malignant stage of cancer development in an animal model (4), which implies that antibody response to these proteins in patients of this study might have existed long before cancer was diagnosed but was suppressed at the time of diagnosis and recovered after radiation and chemotherapy. During the long latency of cancer development, tumor growth and tumor immune response co-exist, which represents an extremely complex interaction between pro-tumor and anti-tumor factors; such factors involve not only diverse elements of innate and adaptive immunity but also tumor per se and its microenvironment. When a tumor progresses to a stage that can be clinically detected, an immune suppressive tumor microenvironment usually develops which includes immunosuppressive tumor-associated macrophages, myeloid-derived suppressor cells, regulatory T cells, and tumor-derived immunosuppressive products (such as VEGF, TGF-β and IL-10) (57). Radiotherapy and chemotherapy could possibly reverse this immunosuppressive tumor microenvironment by eliminating myeloid-derived suppressor (58), regulatory T cells (59), and tumor-derived suppressive factors (60), thus augmenting the pre-existing immune response.

Cell surface membrane proteins are the ideal targets for antibodies. Due to their high hydrophobicity, membrane proteins tend to precipitate at their isoelectric point during isoelectric focusing so that they are difficult to be resolved on a conventional two-dimensional gel electrophoresis used in this study. All the proteins identified in this study are traditionally classified as intracellular proteins. However, although lacking a secretion signal sequence, many proteins can translocate to cell membrane via non-classical pathway under certain patho-biological conditions including cancer where they bind to their partners and exert different functions. In this sense, these "ectopic" proteins could be the more suitable immune targets because they may be absent at the surface of normal cells. As mentioned above, galectin-3 has a membrane form that mediates cell adhesion, migration, and cell-cell interactions (36). Cell surface AnnexinA2 serves as receptor for both tenascin C and tissue plasminogen activator (tPA) which promote tumor angiogenesis and progression (45, 49). Post-translational phosphorylation of AnnexinA2 in pancreatic cancer cells is required for its membrane localization and cell invasion. As a plasminogen receptor, enolase α recruits plasminogen to the cell surface so that fibrinolysis takes place in the vicinity of the cell (50). Such a pericellular fibrinolytic activity facilitates cell's mobility and invasiveness. Indeed, enolase α has been associated with increased venous invasion of hepatocellular carcinoma (51). Increased amount of HSP60 on the cell surface has been seen as "danger signal" for the immune system. Surface HSP60 was found to be associated with alpha3beta 1 integrin which involves in wound healing, tumor invasion and metastasis (52, 53). RhoGDIα is a regulator of Rho GTPases which are involved in a variety of cell signaling pathways (54). RhoGDIα can protect cancer cells from apoptosis induced by chemotherapeutic agents (55) and its overexpression was associated with tumor progression and poor prognosis in colorectal cancer (56).

Antibody response to certain tumor associated antigens (TAAs) was reported to be correlated with tumor burden, thus predicting poor prognosis (14-17). Shebzukhov, et al. reported that antibody response to a SEREX-defined colon cancer TAA, thymidylate synthase, was detected in colon cancer patients only after 5-FU-based chemotherapy and the antibody titer was associated with tumor burden (61). The radio-chemotherapy-enhanced antibody response we observed in this study was clearly associated with a favorable prognosis (FIG. 5). The correlation between antibody titer and tumor burden, if any, was inverse as enolase α specific antibody titer dropped drastically over time in a patient with an early disease relapse (FIG. 5B).

We analyzed humoral immune response in 60 patients with pancreatic ductal adenocarcinoma who had received pancreaticoduodenectomy followed by a combination of an allogeneic GM-CSF-secreting tumor cell vaccination and radiochemotherapy. Antibody response to a variety of vaccine-derived proteins was detected and showed distinct response profiles in different patients. Fourteen antibody-reactive proteins were identified by a serological proteomics approach. Five of the 14 proteins were investigated in detail by ELISA for their antibody response in all 60 patients. Two distinct types of antibody response were observed; one was highly associated with vaccination, suggesting a vaccine-induced response, and the other augmented only by radio-chemotherapy. Both types of antibody response correlated positively with patients' survival, indicating that antibody response to the identified proteins could be a predictor of clinical response. Antibody titer in both types of response declined eventually over time. It may be beneficial to raise and keep antibody titer at high levels by means of adoptively transfusing specific antibodies or actively vaccinating with pure proteins.

We also provide four new findings to support a role for AnnexinA2 in mediating PDAC invasion and metastases. First, the translocation of AnnexinA2 from the cytosol/endosome compartment to the cell membrane is required for AnnexinA2 mediated PDAC cell invasion. Second, phosphorylation at tyrosine 23 is critical for this translocation to occur in PDAC cells. Third, AnnexinA2 translocation in PDAC is mediated by TGF-beta. Fourth, translocation of AnnexinA2 in PDAC is associated with EMT in these cells, further confirming that AnnexinA2 is important to the mechanism by which PDAC cells progress and metastasize.

AnnexinA2 was brought to our attention when we employed the serum from vaccinated patients to screen a panel of tumor antigens targeted by vaccine induced humoral immune responses. Additional studies are underway to determine whether the induction and maintenance of AnnexinA2 humoral responses correlates with improved clinical responses. However, in this study, we focused on characterizing the role of AnnexinA2 in PDAC invasion.

It has been well documented that AnnexinA2 is overexpressed in PDAC in comparison with paracancerous normal pancreatic ductal epithelium (Esposito, Penzel et al. 2006). On IHC analysis of resected patient tumor's from our vaccine study we noted that the cell surface/membrane localization of AnnexinA2 may be a more specific marker for PDAC since this cell surface localized fraction of AnnexinA2 appears to correlate with PDAC pathogenesis. Cell surface AnnexinA2 starts to increase in the PanINs and further increases when the PanINs develop into invasive PDAC. This result is consistent with the reported findings in prostate cancer demonstrating that changes in interferon gamma levels reduces cell surface Annexin 2 expression and also reduces prostate cancer invasion (Hastie, Masters et al. 2008). Furthermore, AnnexinA2 or the AnnexinA2/S100A10 heterotetramer have also been shown to be a high-affinity receptors for multiple extracellular ligands such as tissue plasminogen activator (tPA), plasmin, plasminogen, progastrin/gastrin, tenascin-C, and angiostatin, and all are hypothesized to be mediators of cancer cell invasion and metastases (Kim and Hajjar 2002; Kwon, MacLeod et al. 2005; Sharma and Sharma 2007).

Different subcellular localizations, including membrane, cytoplasmic, and nuclear localizations, have all been reported for AnnexinA2 (Kiln and Hajjar 2002; Rescher and Gerke 2004; Sharma and Shauna 2007; Singh 2007). AnnexinA2 is also secreted extracellularly (Lu, Maeda et al. 2006). The presence of AnnexinA2 in different subcellular fractions is consistent with its multiple functions. It is also likely that AnnexinA2 localizes to different locations in different cell types or under different conditions (Liu, Rothermund et al. 2003; Deora, Kreitzer et al. 2004). AnnexinA2 is sometimes localizes to the cell surface in normal pancreatic ductal epithelium. However, this form of cell surface expression of AnnexinA2 appears to be well organized along the apical surface of the pancreatic ductal epithelium. This is in line with the polarized expression of AnnexinA2 in many normal tissue types (Massey-Harroche, Mayran et al. 1998) and supports the requirement of AnnexinA2 for the formation of the apical surface and lumen in the three-dimensional Madin-Darby canine kidney cell system, which is a model of kidney development. By contrast, the polarized expression of AnnexinA2 is disrupted in PanINs and PDAC, even though the lumen structure is still maintained in these lesions. Similar findings were observed in the Kras/p53 mutation conditional knock-in mice that spontaneously develop PDAC (Hingorani, Wang et al. 2005). It remains to be explored whether the disruption of the polarized expression of AnnexinA2 on the PDAC cell surface mediates PDAC cell invasion, or if it is only the consequence of overexpression of AnnexinA2 on the cell membrane.

We did not repeat the same IHC analysis as previously described by others for AnnexinA2. Instead, we created a score system to measure the cell surface/membrane staining of AnnexinA2 in IHC specimens. Similar score systems have been used in evaluating other tumor markers such as HER-2/neu in IHC specimens to correlate expression levels with pathogenesis (Wolff, Hammond et al. 2007). This IHC analysis on paraffin-embedded tissue blocks provides a semi-quantitative method for approximating changes in AnnexinA2 expression and translocalization from the cytosol to the cell surface/membrane in cancer of the pancreatic duct (PDAC). Further studies are required to validate this method for correlating AnnexinA2 cell surface/membrane translocation with the prognosis of PDAC.

The results below demonstrate that tyrosine phosphorylation of AnnexinA2 regulates the translocation of AnnexinA2 from the cytosol compartment to the membrane/cell surface in PDAC. A number of tyrosine kinases have previously been implicated in regulating the function of AnnexinA2 in other types of cancer cells. Until now, it was not known which tyrosine kinase (s) were responsible for the phosphorylation of AnnexinA2 in the process of cell surface translocation. The fact that the Y23E mutated AnnexinA2 maintained all the other functions of wild-type AnnexinA2 suggests the point mutation itself does not abolish the function of AnnexinA2. However, it does show that the unphosphoryylated AnnexinA2 at Tyr23, is unable to translocate to the cell surface/membrane and therefore suppresses the invasion capacity of PDAC cells. It remains to be explored whether tyrosine phosphorylation of AnnexinA2 directly regulates PDAC invasion or indirectly through regulating the membrane/cell surface translocation of AnnexinA2.

In addition, the results below provide evidence that AnnexinA2 translocation to the cell surface/membrane in PDAC is mediated by TGF-beta. We also show that the translocation of AnnexinA2 in PDAC is associated with EMT in these cells as characterized by the downregulation of epithelial cell markers and the upregulation of mesenchymal cell markers. AnnexinA2 has previously been shown to mediate TGFβ-activated EMT in cardiac valve development during embryogenesis (Krishnan, Deora et al. 2004). The EMT is a highly conserved normal cellular program that allows polarized, immotile epithelial cells to convert to motile mesenchymal cells during organ development. This important process was initially recognized as a critical stage of embryonic development but has more recently been implicated in promoting carcinoma invasion and metastasis (Weinberg 2008). Several inducers of the normal EMT process are transcription factors that repress E-cadherin expression, such as Snail, Slug, and Twist. Interestingly, it has been demonstrated by others that the transcription factors Snail and Slug are expressed in PDAC but not in normal tissue (Hotz, Arndt et al. 2007). Furthermore, the expression of E-cadherin, an epithelial marker, has been shown to be suppressed in PDAC, and the expression of N-cadherin, a mesenchymal marker, induced in PDAC (Natalwala, Spychal et al. 2008). It has also been suggested that loss of Smad4 expression in PDAC can lead to the aberrant activation of STAT3, which may contribute to the switch of TGFβ from a tumor-suppressive to a tumor-promoting EMT pathway in PDAC (Zhao, Venkatasubbarao et al. 2008). However, current knowledge on EMT is limited to its characteristic transcription circuit. It is still unknown how cancer cells functionally interact with extracellular matrix, invade the basement membrane and migrate to distant locations when the EMT is initiated. Thus, our data provide a new role for AnnexinA2 as a mediatior of the cancer-stroma interaction, and as a molecule involved in the initial steps of PDAC invasion and metastases.

Taken together, the results described below support AnnexinA2 as a biomarker of and immunogenic protein expressed by PDAC. Moreover, the results below support a role for cell surface AnnexinA2 in PDAC invasion, and supports the development of AnnexinA2 as a novel PDAC therapeutic target.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Antibody Response Signature in Vaccinated Patients

Here we report on antibody response in serum samples collected before and after vaccination which is specific for proteins extracted from the tumor vaccine lines. We found that not only did most of the patients who survived longer than 3 years develop an antibody response in their post-vaccination sera, but they showed the highest number of antibodies specific for a variety of proteins of different sizes. Using a proteomics approach, we identified a panel of proteins for which specific antibody titers were elevated in the post-vaccination serum samples, which translated to a favorable clinical outcome.

Figure 1:
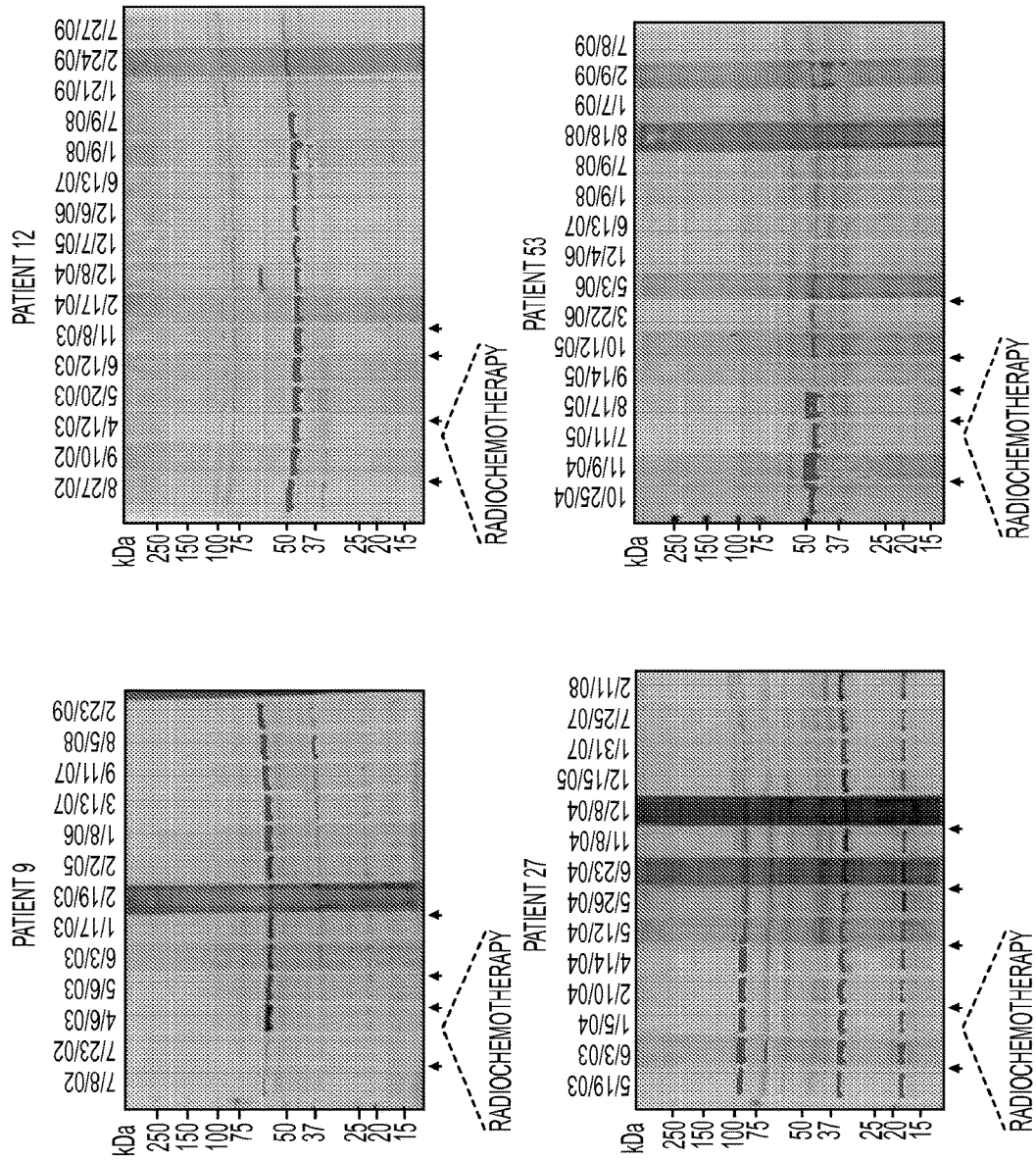
FIG. 1. Chronological Changes of Vaccine-Specific Antibody Response in Four Patients.

Study design and clinical evaluation of a phase II trial on an allogeneic GM-CSF secreting pancreatic tumor vaccine were published elsewhere (28). Briefly, 60 patients with stage 1, 2, and 3 resected PDA were enrolled. First vaccination was administered 8 weeks after pancreaticoduodenectomy and followed 1 month later by a 6-month course of radiation and 5-FU-based chemotherapy. One month after radiation and chemotherapy, 3 more vaccinations were given at an interval of 1 month and a boost $5^{th}$ vaccination at 6 month after the $4^{th}$ vaccination. Serum samples were collected pre-vaccination, 14 days after $1^{st}$ and 28 days after each subsequent vaccination. First, we set out to look into chronological changes of vaccine-specific antibody response. To this end, we analyzed by Western blotting of total vaccine cell lysate with serum samples collected at all time points from 4 patients who have survived greater than 5 years. FIG. 1 shows that each patient had a different but distinct antibody response profile in which antibody activities were seen against a fix set of proteins of different sizes for all the time points with one or two dominant responses. A few antibodies showed up only in the post-vaccination sera but, more often, titer of antibodies changed in the post-vaccination or post-radio-chemotherapy sera.

Example 2—Antibody Response Correlates with Favorable Clinical Response

The above Western blot result also showed that the highest number of antibody-reactive protein bands, though not necessary the highest antibody titer, was observed when probed with sera collected after $3^{rd}$ vaccination (FIG. 1). To expand the analysis to all 60 patients, serum samples collected at pre-vaccination (60 patients) and post-$3^{rd}$ vaccination (33 out of 60 patients) were tested for vaccine-specific antibody response using Western blot analysis. Serum samples from 22 healthy donors were also included as controls. Sixty vaccinated patients were divided into 3 groups based on survival. Group A (n=12) are patients who completed all vaccine schedule and survived greater than 3 years at the end of this trial. Majority of patients in this group developed antibody response in their post-vaccination sera as demonstrated by either appearance of new antibody activities or an elevated titer of existing antibody activities (FIG. 2A). In contrast, very few developed antibody response in group B patients (n=21) who completed at least 3 vaccinations but suffered from disease relapse and survived less than 3 years (FIG. 2B). Furthermore, in patients who developed an antibody response, those in group A showed a higher number of antibodies specific for a variety of proteins of different sizes compared to those in group B. Because no post-vaccination sera available in group C patients (n=27) who completed only $1^{st}$ vaccination followed by an early disease relapse, pre-vaccination serum samples were analyzed. In terms of pre-existing antibody response to the vaccine, no obvious difference was observed between group C patients and group D (n=22) healthy donors with no history of cancer (FIGS. 2C and 2D).

Example 3—Identification of Antibody-Reactive Proteins by Proteomics

We used a serological proteomics approach to identify the antigens that could be recognized by antibodies detected in serum samples from clinical responders. To reduce sample complexity and to enrich low abundant proteins, we pre-fractionated total cell lysate on a ZOOM IEF Fractionator (Invitrogen) into 2 fractions which contained proteins with isoelectric points (pI) from pH 3-6 and from pH 7-10, respectively. Each fraction was further subject to 2-dimensional electrophoresis (2-DE) and immunoblotting analysis with pre-versus post ($3^{rd}$ vaccine)-vaccination serum samples from the 4 long-term survivors (patients 9, 12, 27 and 53). Corresponding antibody-reactive protein spots on Coomassie bright blue (CBB)-stained gels were excised and digested with trypsin. Resulting peptides were analyzed by matrix-assisted laser desorption ionization time-of-flight (MALDI-TOF) mass spectrometry. A representative result from patient #9 was shown in FIG. 3. Table 1 summarizes the antibody-reactive proteins identified with serum samples from all the 4 patients. Fourteen proteins were identified with higher antibody titer in post-vaccination versus pre-vaccination sera from 1 or 2 patients. These proteins are of different functions, many of which are critical for cell growth and differentiation. Many proteins in this list have been reported to be overexpressed in cancers of different tissue types including pancreatic cancer (29-33). Next, we cloned genes coding for the proteins from the vaccine lines and made recombinant proteins in a mammalian expression system. We used the purified recombinant proteins as antigens to test all 60 patients' serum samples by ELISA to see whether other patients on the trial also developed antibody response to these proteins and how the antibody titer changed over the course of vaccinations. So far, we have completed analysis of five proteins as reported below.

Example 4—Galectin-3-Specific Antibody Response Correlates with Vaccinations and Clinical Outcome Sera from 3 of the 4 patients could detect galectin-3 with an elevated antibody titer in their post-vaccination sera in the above serological proteomics study (Table 1). When all patients were tested by ELISA, only a few showed a pre-existing antibody response to galectin-3 in their pre-vaccination sera while majority of the patients had a very low level of antibody titer and there is no difference in different groups (FIG. 4A). A few serum samples from healthy donors also showed antibody activity to galectin-3, but as a group the antibody titer was not different from that of patients (FIG. 4A). Because no post-vaccination serum samples were available from patients who received only single vaccination, we compared antibody titer changes over the course of vaccination between patients with disease-free survival>3 years (DFS>3yr) and those with DFS<3yr. As shown in FIG. 4B, 7 out of 12 patients (58%) in DFS>3yr group had a greater than 2-fold antibody titer increase in their post-vaccination sera whereas only 2 out of 21 patients (9.5%) in DFS<3yr showed an antibody titer increase (indicated in solid symbols). Antibody titer started to rise just after $1^{st}$ vaccination in 4 of the 8 patients in DFS>3yr group who had an elevated antibody response in post-vaccination sera, but dropped slightly after radiation and chemotherapy, and after $2^{nd}$ vaccination the antibody titer resumed to the post-$1^{st}$ vaccination level and peaked after $4^{th}$ vaccination (FIG. 4C in solid symbols and solid lines). Three patients received a $5^{th}$ (boost) vaccination 6 months later, 2 of whom showed a slight decrease in antibody titer post-$5^{th}$ vaccination. The other 3 patients in the DFS>3yr group (FIG. 4C in open symbols and dashed lines) showed a delayed galectin-3 antibody response which occurred after 3 vaccinations. It is worthy to note that patient 9, who failed to detect galectin-3 in the proteomics study because no elevated galectin-3 antibody was detected in the post-$3^{rd}$ vaccination serum by immunoblotting, had a high pre-existing galectin-3 antibody response which dropped dramatically post radiation and thermotherapy and did not resume to pre-vaccination level until after $3^{rd}$ vaccination (FIG. 4C). These results demonstrated that anti-galectin-3 antibody response could be induced in pancreatic cancer patients receiving allogeneic GM-CSF secreting tumor vaccine and that this galectin-3- specific antibody response correlates with a favorable clinical outcome. In addition, radiation and chemotherapy could suppress galectin-3 antibody response.

relative to enolase α antibody in patient 10) of pre-existing antibodies to AnnexinA2 and HSP60 but negative for RhoGDIα antibody in pre-vaccination serum. Antibody

TABLE 1

Antibody-reactive proteins identified by serological proteomics

| Protein accession | Gene symbol | Protein description | Protein function | Patients with Ab response |
|---|---|---|---|---|
| gi\|4757756 | ANXA2 | AnnexinA2 isoform 2 | Calcium-dependent phospholipid-binding protein regulating cell growth, signal transduction, and membrane physiology | 9, 27 |
| gi\|4502551 | CALU | Calumenin isoform A precursor | Calcium-binding protein involving in protein folding and sorting in ER | 9 |
| gi\|31542947 | HPSD1 | Chaperonin (heat shock protein 60) | Essential for folding and assembly of newly imported proteins in mitochondria | 9 |
| gi\|4503571 | ENO1 | Enolase 1 or α | Glycolytic emzyme | 9, 12 |
| gi\|115430223 | LGALS3 | Galectin 3 | Galactoside-binding protein with pleiotropic functions including inhibition of T cell activation | 12, 27, 53 |
| gi\|24234699 | KRT19 | Keratin 19 | Cytoskeletal protein | 12, 53 |
| gi\|5031857 | LDHA | Lactate dehydrogenase A isoform 1 | LDH M isozyme in anaerobic glycolysis | 9, 27 |
| gi\|109148508 | OTUB1 | Otubain 1 | Ubiquitin iso-peptidase | 27 |
| gi\|10863927 | PPIA | Peptidylprolyl isomerase A | Cyclosporin-binding protein | 9, 27 |
| gi\|20070125 | P4HB | Prolyl 4-hydroxylase, beta subunit precursor | Subunit of a multifunctional protein disulfide isomerase | 9 |
| gi\|33286418 | PKM2 | Pyruvate kinase, muscle isoform M2 | Glycolytic enzyme | 9, 27 |
| gi\|4757768 | ARHGDIA | Rho GDP dissociation inhibitor (GDI) alpha | Regulator of Ras related GTP-binding protein signaling pathways | 9 |
| gi\|14389309 | TUBA1C | Tubulin alpha 6 | Cytoskeletal protein; microtubule formation | 53 |
| gi\|4507669 | TPT1 | Tumor protein, translationally-controlled 1 | Anti-apoptotic and chaperon-like protein | 27 |

Example 5—Enhancement of Certain Antibody Response by Radiation and Chemotherapy Like galectin-3 specific antibody response, antibody response to AnnexinA2, enolase α, heat shock protein 60 (HSP60), or Rho GDP dissociation inhibitor a (RhoGDIα) in pre-vaccination sera showed no difference among 3 groups of vaccinated patients and healthy donors (FIG. 5A, left panel). Unlike the broad antibody response to galectin-3, an elevated antibody titer to these 4 proteins in post-vaccination sera was observed in only 1 or 2 patients (8.3%~9.5%) in the DFS>3yr group and none in the DFS<3yr group (FIG. 5A, right panel). Most strikingly, in the 3 patients (patients 9, 10, and 47) who developed an antibody response, vaccine could not induce antibody response to any of the 4 proteins. Instead, antibody titer arose abruptly after the 6 months of radiochemotherapy and then declined over time (FIG. 5B). The most robust antibody response was that against enolase α in patient 10 who had a high pre-existing enolase α antibody titer which increased further to more than 3-fold higher post radiochemotherapy than pre-vaccination. The antibody titer started declining after $3^{rd}$ vaccination and reached almost the pre-vaccination level after $4^{th}$ vaccination. Patient 6 from DFS<3yr group also had a high pre-existing enolase α antibody titer, but the titer dropped drastically over time to the lowest level after $3^{rd}$ vaccination when disease relapsed. Patient 9 had medium level (in titers in patient 9 to all 3 proteins increased more than 2-fold post radiochemotherapy and kept relatively stable up to post $4^{th}$ vaccination (the last vaccination for patient 9). Antibody titers to AnnexinA2 and HSP60 also increased dramatically post radiochemotherapy in patient 47, declined gradually afterwards and returned to the pre-vaccination level after $5^{th}$ vaccination.

Example 6—Intact Antibody Response to Influenza Proteins in Vaccinated Patients To rule out the possibility of a compromised general immunity developed in the vaccinated patients which could affect tumor-specific immune response, we used a fusion protein NPM1 which contains two highly-conserved influenza proteins, nucleoprotein (NP) and matrix protein (M1), as antigen to assess the general immunity status since seasonal flu is a common condition in the public population. As shown in FIG. 6A, influenza NPM1-specific antibody response in vaccinated patients was not different from that in healthy donors. Different groups of patients also showed a similar degree of antibody response to influenza. In addition, influenza antibody response kept relatively stable over the course of tumor vaccination (FIG. 6B). In those patients who developed antibody response to tumor-derived proteins, their influenza antibody response was affected neither by tumor vaccinations nor by radiation and chemotherapy (FIG.

6C). This result indicates that immune response to common infectious agents in cancer patients is intact, which is in accordance with a report on intact T cell response to cytomegalovirus and influenza virus in colorectal cancer patients (34).

Example 7—Methods for Examples 1-6

Patients and Serum Samples

Blood samples were collected from all 60 patients who received an allogeneic GM-CSF-secreting pancreatic tumor vaccine at different time points (pre-vaccination, 14 days after $1^{st}$ vaccination, and 28 days after the subsequent vaccinations) and 22 healthy donors with no history of cancer following informed consent as part of the recently completed phase II clinical trial (28). Sera were separated from the whole blood by centrifugation and frozen in aliquots at −80° C. until assayed.

Cell Lines

Pancreatic cancer cell lines PANC 10.05 and PANC 6.03 were derived from two histologically confirmed primary pancreatic adenocarcinomas. Vaccine cell lines used in the clinical trial were developed by genetically modifying these two cell lines to secrete human GM-CSF (62). To minimize tumor antigen changes caused by the introduction of GM-CSF, the unmodified parental cell lines were used in the present study as a source of antigens for testing immune response. The cell lines were cultured as described previously (62).

SDS-PAGE Electrophoresis and Western Blotting

Total cell lysate was prepared by lysing PANC 10.05 and PANC 6.03 cells in lysis buffer (50 mM Tris-Cl, pH 8.0, 150 mM sodium chloride, 0.5% sodium deoxycholate, 0.2% sodium dodecyl sulfate, and 0.02% sodium azide) supplemented with protease inhibitor cocktail (Sigma) and 1 mM PMSF. Protein concentration was determined by BCA assay (Pierce Biotech). Proteins in the lysate were resolved at 40 μg/lane on Criterion XT 4-12% Bis-Tris precast gels (Bio-Rad) in MOPS running buffer. Blots were transferred to Hybond ECL 0.2 μm nitrocellulose membrane (GE Healthcare) in Towbin transfer buffer. Membrane was blocked in 5% BSA in 0.1% Tween 20-TBS (TBS-T) buffer for 1 h at room temperature and probed with 1:1,000 dilution of serum at 4° C. overnight. Antibody of IgG class was detected by incubating the membrane with 1:100,000 dilution of goat anti-human IgG (γ-chain specific) peroxidase conjugate (Sigma, A8419) for 1 h at room temperature and then ECL Western Blotting Detection Reagents (GE Healthcare) for 1 min at room temperature. Chemiluminescent signals were detected on a Molecular Imager ChemiDoc XRS system with Quantity One software (Bio-Rad).

Two-Dimensional Electrophoresis (2-DE)

Cell lysate for 2-DE was prepared by lysing PANC 10.05 and PANC 6.03 cells in isoelectric focusing (IEF) buffer (7 M urea, 2 M thiourea, 4% CHAPS, 20 mM DTT, and 0.5% carrier ampholytes, pH3-10). Protein concentration was estimated by Bradford assay. Cell lysate was pre-fractionated on a ZOOM IEF Fractionator (Invitrogen) into 2 fractions which contained proteins with isoelectric points from pH 3-6 and from pH 7-10, respectively by following manufacturer's instruction manual. Each fraction with 20 μg (for immunoblotting) or 40 μg of proteins (for Coomassie protein staining) was loaded onto 7 cm ReadyStrip IPG strips (Bio-Rad), pH4-7 (for fraction pH 3-6) or pH7-10 (for fraction pH7-10). First dimension IEF was carried out on a ZOOM IPGRunner system (Invitrogen) using the following voltage ramp protocol: 175 V for 15 minutes, 175-2000 V ramp for 45 minutes, and 2,000 V for 105 minutes. For the second dimension, focused IPG strips were equilibrated in XT sample buffer (Bio-Rad) in the presence of XT Sample Reducing Agent (Bio-Rad) for 15 minutes, and further incubated in XT sample buffer in the presence of 125 mM iodoacetamide for 15 minutes. The strips were placed on 12% XT Bis-Tris precast gels (Bio-Rad) and embedded in 0.5% agarose. The gels were run in MOPS buffer at 150V for 1 h 20 min and stained for protein with SimplyBlue SafeStain Coomassie G-250 (Invitrogen). For immunoblotting, proteins in the gels were transferred to Hybond ECL 0.2 μm nitrocellulose membrane (GE Healthcare) and probed with patients' sera as described above.

Mass Spectrometry

Protein spots on the Coomassie-stained gels corresponding to the antibody-reactive proteins revealed on the images of Western blot analysis were excised. Trypsin in-gel digestion was performed using Trypsin Profile IGD Kit (Sigma) as instructed in manufacturer's manual. The resulting peptide mixture was cleaned up with a ZipTip $C_{18}$ pipette tip (Millipore) and eluted directly onto a MALDI sample plate in 2 μl of MALDI matrix of 10 mg/ml of a-cyano-4-hydroxycinnamic acid in 70% acetonitrile with 0.1% trifluoroacetic acid. MALDI-TOF MS analysis was performed in reflection positive ion mode on a Voyager-DE STR System (Applied Biosystems). Protein identity was obtained by searching the monoisotopic masses against the NCBInr database at a tolerance of 100 ppm using Mascot Peptide Mass Fingerprint online search engine (matrixscience.com).

Expression and Purification of Recombinant Proteins

Genes coding for the identified proteins were cloned from either PANC 10.05 or PANC 6.03 cells with a TOPO TA cloning kit (Invitrogen). NPM1 cDNA was amplified by PCR from plasmid pNPM1 NS1 (kindly provided by Dr. Alexander M. Shneider) which contains viral NP and M1 sequences from influenza strain A/WSN/33-H1N1 (63). A fusion gene with an 8×His tag sequence at the 3'-terminus was inserted into a mammalian expression vector pcDNA3.3-TOPO (Invitrogen). The 8×His tagged recombinant protein was transiently expressed in 293T cells by transfecting the cells with the protein-coding vector by Lipofectamine 2000-mediated method (Invitrogen) and purified with H is GraviTrap Prepacked Ni Sepharose affinity column (GE Healthcare) per manufacturer's instruction. The purity of the protein was confirmed by SDS-PAGE analysis, Western blotting with a few selected serum samples, and MALDI-TOF MS.

ELISA

Costar 3690 96-well half-area EIA/RIA plates (Corning) were coated with 30 μl/well of purified recombinant proteins at 5 μg/ml (galectin-3, HSP60, RhoGDIα, and NPM1) or 10 μg/ml (AnnexinA2 and enolase α) in bicarbonate/carbonate coating buffer at 4° C. overnight. The protein-coated plates were incubated with 150 μl/well of ELISA Blocker Blocking Buffer (Pierce Biotech) for 1 h at room temperature. The wells were then incubated with 30 μl/well of serial dilutions (1:100, 1:200, 1:400, and 1:800) of sera (duplicates for each dilution) for 2 h at room temperature and with 30 μl/well of 1:200,000 dilution of goat anti-human IgG (γ-chain specific) peroxidase conjugate (Sigma, A8419) for 1 h at room temperature. The wells were washed extensively with TBS-T between incubations. Finally, 30 μl/well of ready-to-use 3,3'5,5'-tetramethylbenzidine (TMB) liquid substrate (Sigma, T0440) was added to the wells and incubated in dark for 20 min at room temperature. The color development was stopped by adding to the wells 30 μl/well of 1N sulfuric acid. Absorbance at 450 nm (with a reference wavelength of 570 nm) was measured on a PowerWave 340 microplate reader (BioTek). For each protein, an ELISA optimization was performed in advance with a positive serum sample (based on Western blot analysis) to have an $OD_{450}$ of about 1.000 at serum dilution of 1:100. For each experiment, a control ELISA was performed simultaneously with a second set of plates coated with only coating buffer for background subtraction. Antibody titer in a serum sample was reported as $OD_{450}$ at serum dilution of 1:400 after background subtraction.

Example 8—Identification of AnnexinA2 as a Potential Tumor Associated Antigen and Biomarker of PDAC In this report we describe the development of a functional proteomic approach to identify immune relevant proteins that are recognized by sera from vaccinated patients who have demonstrated a prolonged disease free and overall survival. Immunized sera was used to screen a panel of proteins isolated by a combination of two dimensional electrophoresis (2-DE) and mass spectrometry. Using this approach, we have identified AnnexinA2 as a new candidate tumor antigen that may be involved in PDAC development and progression. Specifically, we show that cell cytoplasmic to cell surface/membrane translocation of AnnexinA2 occurs with PDAC development and progression, and occurs as a result of the phosphorylation of tyrosine 23 on AnnexinA2. We also show that the translocation of AnnexinA2 plays an important role in PDAC invasion and that loss of AnnexinA2 translocation to the cell membrane leads to loss of TGFβ-induced EMT in pancreatic cancer cells.

We have developed a functional proteomic approach that employs the sera from surgically resected pancreatic cancer patients treated in a recently completed phase II clinical trial of an allogeneic GM-CSF-secreting pancreatic tumor vaccine. Specifically, we used the immunized sera from two subjects who demonstrated other evidence of post-vaccination immune responses to screen whole cell extracts from the two vaccinating cell lines which serve as the proteome. Proteins within the extracts were separated by two dimensional electrophoresis (2-DE) and immunoblots were performed to compare recognition by pre- and post-vaccination sera isolated from a subset of treated patients. The proteins that were found to be unique in the post-vaccination immunoblots were identified by mass spectrometry (Huang et al., unpublished data). AnnexinA2 is one protein that was found to be recognized by post-vaccination sera from both patients evaluated. To further evaluate the prevalence of post vaccination humoral responses to AnnexinA2, purified recombinant AnnexinA2 from mammalian cells was first produced and confirmed to be pure by Coumassie blue stain (FIG. 7A), and then used to screen pre-vaccination and post-vaccination serum from 16 patients treated in this phase II clinical trial by western blot (FIG. 7B). As summarized in Table 2, vaccine induced anti-AnnexinA2 antibody was detected in 6 of 8 patients who demonstrated an overall survival longer than 36 months (Lutz et al. Manuscript submitted), and only in 1 of the other 8 patients who did not demonstrate long-term survival. This result provides the first evidence that AnnexinA2 is a potential pancreatic cancer tumor associated antigen. The correlation between anti-AnnexinA2 antibody induction at multiple time points and patient survival remains to be further explored in all 60 patients treated in this phase II study.

TABLE 2

Correlation between vaccine-induced anti-AnnexinA2 antibody response and patients' survival

| Patient ID | Disease Status | Overall Survival Time (Mo)* | Increased Anti-ANXA2 antibody response |
|---|---|---|---|
| 3.009 | Disease free | >36 | + |
| 3.010 | Disease free | >36 | − |
| 3.012 | Disease free | >36 | − |
| 3.016 | Disease free | >36 | + |
| 3.027 | Disease free | >36 | + |
| 3.028 | Disease free | >36 | + |
| 3.031 | Disease free | >36 | + |
| 3.041 | Recurrent | >36 | + |
| 3.023 | Recurrent | <36 | − |
| 3.032 | Recurrent | <36 | − |
| 3.025 | Recurrent | <36 | + |
| 3.033 | Recurrent | <36 | − |
| 3.039 | Recurrent | <36 | − |
| 3.001 | Recurrent | <36 | − |
| 3.004 | Recurrent | <36 | − |
| 3.037 | Recurrent | <36 | − |

*Overall survival is defined as the time from surgery until death or until the last follow up on Apr. 21, 2008; Mo, month.

Example 9—Cell Surface AnnexinA2 is Critical for Pancreatic Cancer Cell Invasion AnnexinA2 is reported to be overexpressed in a variety of cancers including PDAC when compared with normal tissues (Vishwanatha, Chiang et al. 1993; Esposito, Penzel et al. 2006). Normal pancreatic ductal epithelial cells usually show weak cytoplasmic and lumenal staining of AnnexinA2 by immunohistochemistry (IHC) analysis. We analyzed the pattern of expression in tumor cells by IHC in resected tumors of 40 of the 60 patients treated in our Phase II study for whom specimens were available for staining. Consistently, we found that cell-surface expression of AnnexinA2 is increased in the majority of pancreatic tumor tissues analyzed. We used the scores of 0 to 3 to measure the different intensities of cell-surface staining of AnnexinA2, with a score of 0 representing no staining and a score of 3 representing the strongest staining (FIG. 7C-7E). We excluded cytoplasmic and luminal staining in our score system and only measured the intensity of AnnexinA2 expression on the cell surface. PDAC cells vary in their AnnexinA2 expression level within the same tumor tissue (FIG. 7E). Therefore, we estimated the percentage of PDAC cells at each score level and calculated the average score of each pancreatic tumor tissue by multiplying each score by their percentages (see Methods). None of the normal appearing ductal epithelial cells within the resected tumor masses express 3+ AnnexinA2 and few express 2+ AnnexinA2 (FIG. 7D). Thus, if an average score of a pancreatic tumor tissue is 1.5 or above, cell surface expression of AnnexinA2 in the tumor tissue was considered significantly increased. Thus, 29 (72.5%) out of 40 pancreatic tumor tissue samples tested have a significantly increased cell surface expression of AnnexinA2. We have repeated IHC in an additional 16 pancreatic tumor tissues and scored them blindly. Similar scores were obtained each time demonstrating the reproducibility of this scoring system. Moreover, cell-surface localized AnnexinA2 appears to increase in the progression from PanIN lesions to PDAC by IHS (FIG. 7C-D). This result is consistent with a previous report suggesting that cell-surface localized AnnexinA2 may play a role in the progression from pre-malignant to malignant pancreatic cancers (Vishwanatha, Chiang et al. 1993; Esposito, Penzel et al. 2006).

Further studies are needed to determine whether increased expression of cell surface AnnexinA2 correlates with the prognosis of PDAC.

Example 10—AnnexinA2 Mediates the Invasion of Pancreatic Cancer Cells

A number of physiological roles have been proposed for AnnexinA2, including membrane fusion, cell adhesion, and cell proliferation (Kim and Hajjar 2002; Rescher and Gerke 2004; Sharma and Sharma 2007; Singh 2007). AnnexinA2 mainly binds membrane associated phospholipids and cytoskeleton, and is also associated with the extra-cellular surface of cells, functioning as a high-affinity receptor for multiple ligands such as tissue plasminogen activator (tPA), plasmin, plasminogen, progastrin/gastrin, tenascin-C, and angiostatin. These extracellular molecules have been implicated in PDAC development, invasion, and the metastatic process (Kim and Hajjar 2002; Rescher and Gerke 2004; Sharma and Sharma 2007; Singh 2007). Therefore, to test whether AnnexinA2 is involved in PDAC invasion, we knocked down the expression of AnnexinA2 in PDAC cells by siRNA and evaluated its ability to demonstrate invasion through a BME (basement membrane extract)-coated transwell in an in vitro invasion assay (FIG. 8A). As shown in FIG. 8B, knock-down of AnnexinA2 suppressed the in vitro invasion of PDAC cells. These data have been confirmed in two independent PDAC cell lines derived from primary PDAC tumors.

The induction of antibodies against AnnexinA2 in vaccinated patients with a good survival (FIG. 7B) suggests that anti-AnnexinA2 antibodies may have an anti-tumor effect. Although such an effect may be mediated by antibody-dependent immunity, a direct inhibitory effect on the function of AnnexinA2 cannot be excluded. To test the hypothesis, we incubated the PDAC cells with polyclonal anti-AnnexinA2 antibodies. Our data demonstrate that an anti-AnnexinA2 antibody can specifically inhibit the in vitro invasion of PDAC cells (FIG. 8C).

Example 11—Cell Surface Localization of AnnexinA2 is Critical for PDAC Cell Invasion Next, we investigated whether over expression of AnnexinA2 is a regulatory mechanism that confers PDAC cells with invasion capacity. We first found that different pancreatic cancer cells vary in their invasion capacity (FIG. 9A). Of the 11 PDAC cell lines tested, 8 of these cell lines have higher invasion capacity and 3 have lower invasion capacity when compared with a normal fibroblast cell line. We then examined the proliferation rates of selected cell lines and did not appreciate any correlation between their proliferation rate and invasion capacity (data not shown). Next, we examined whether different levels of expression of AnnexinA2 in the whole cell extract from these cells correlated with their invasion capacity. As shown in FIG. 9B, expression of AnnexinA2 is slightly lower in cells with lower invasion capacity and slightly higher in those with higher invasion capacity, suggesting that over expression of AnnexinA2 in PDAC may contribute to the pancreatic cancer cell's greater invasion potential. Nonetheless, expression levels of AnnexinA2 in whole cell extracts vary to a much less extent than the invasion capacity, suggesting that other regulatory mechanisms play a dominant role in determining the invasion capacity of PDAC cells.

In an attempt to uncover other regulatory mechanisms that account for the invasion capacity of PDAC cells, we examined the subcellular localization of AnnexinA2 in various pancreatic cancers by fluorescent staining with anti-AnnexinA2 antibodies. The immunostaining of AnnexinA2 in representative cells with higher or lower invasion capacity is shown in FIG. 9C. Interestingly, as shown in Table 3, AnnexinA2 is predominantly localized to the cell membrane in all 8 PDAC cell lines tested with higher invasion capacity. In contrast, AnnexinA2 is found localized to the cytoplasm and/or nucleus in the 2 out of 3 pancreatic cancer cells tested with lower invasion capacity and in the non-cancerous fibroblast cell line.

TABLE 3

Cell Surface Localization of AnnexinA2 in Cells with Different Invasive Capacities.

|  | Cell lines | Cell Surface Localization of AnnexinA2 |
|---|---|---|
| High invasive capacity | Panc10.05 | + |
|  | Panc01.28 | + |
|  | Panc2.8 | + |
|  | Panc2.03 | + |
|  | Panc4.03 | + |
|  | TS0129 | + |
|  | Panc2.13 | + |
|  | Panc2.43 | + |
| Low invasive capacity | Panc3.11 | − |
|  | Panc9.3.96 | − |
|  | Panc6.03 | + |
|  | Fibroblast Cells | − |

Example 12—Phosphorylation of AnnexinA2 at Tyrosone 23 is Critical for its Localization to the Cell Surface A published study has suggested that AnnexinA2 is phosphorylated at Tyrosine 23 (Tyr23) when it is localized to the cell surface under stress (Deora, Kreitzer et al. 2004). Malignant cells often mimic normal cells that have been subjected to a variety of stress stimuli. We therefore hypothesized that AnnexinA2, when localized to the cell surface of PDAC cells is also a tyrosine phosphoprotein. To test our hypothesis, we eluted the cell surface fraction of AnnexinA2 from the Panc10.05 PDAC cells which have a high invasion capacity. We found that the cell surface fraction of the AnnexinA2 protein is in fact a tyrosine phosphorylated protein, when detected using the anti-phosphotyrosine antibody (FIG. 10A). In contrast, AnnexinA2 is not eluted from the cell surface of Panc 3.11 cells, which is one of the PDAC cell lines that demonstrated lower invasion capacity.

It has long been known that AnnexinA2 is a major substrate for the Src kinase, and this kinase phosphorylates AnnexinA2 in vivo at the Tyr23 residue (Sharma and Sharma 2007). To test whether phosphorylation of AnnexinA2 at Try23 plays any role in its localization to the cell surface, we generated a panel of lentivirus vectors expressing either the exogenous AnnexinA2 (LV-ANXA2WT), the AnnexinA2 protein in which we created a point mutation (Y23A) to change Tyr23 to an alanine to abolish the tyrosine phosphorylation site on exogenous AnnexinA2, or the AnnexinA2 protein in which we created a point mutation (Y23E) to change Tyr23 to glutamic acid to mimic constitutive phosphorylation. We used these lentivirus vectors to infect Panc10.05 cells and then performed anti-AnnexinA2 immunostaining. As shown in FIG. 10B, AnnexinA2 localized to the cell surface in uninfected Panc10.05 cells and Panc10.05 cells infected by the lentiviruses expressing either ANXA2WT or the mutant ANXA2Y23E. In contrast, AnnexinA2 localized to the cytoplasm in Panc10.05 cells infected with the lentivirus expressing the mutant protein, ANXA2Y23A. It should be noted that immunostaining of Annex in A2 detected both exogenous and endogenous AnnexinA2 at the same time. Even the endogenous AnnexinA2 no longer localized to the cell surface in the cells infected with LV-ANXA2Y23A, suggesting that ANXA2Y23A had a dominant negative effect.

To specifically show the localization of exogenously expressed AnnexinA2, we transfected Panc10.05 cells with a previously described plasmid expressing AnnexinA2 that was carboxyl-terminally tagged by GFP (Merrifield, Rescher et al. 2001). Consistent with this previous report, the ANXA2WT-GFP localized to the cell surface of PDAC cells (FIG. 10C). Next, we transfected Panc10.05 cells with the plasmid expressing GFP-tagged AnnexinA2 with the Y23A mutation (ANXA2Y23A-GFP) and found that ANXA2Y23A-GFP localized to the cytoplasm (FIG. 10C). By contrast, Panc 10.05 cells transfected with the plasmid expressing ANXA2Y23E-GFP localized to the cell surface. Taken together, these data demonstrate that phosphorylation at Try23 is critical for the localization of AnnexinA2 to the cell surface.

Example 13—Tyrosine 23 Phosphorylation and Cell Surface Localization of AnnexinA2 are Required for Invasion by PDAC Cells Our data show that Try23 phosphorylation of AnnexinA2 affects the localization of AnnexinA2. To address whether the change in AnnexinA2 localization that occurs as a consequence of Try23 phosphorylation affects the invasion capacity of PDAC cells, we developed a set of plasmids that express exogenous AnnexinA2. The expressed exogenous AnnexinA2 is resistant to RNA interference because of mutations within the siRNA target site when these plasmids are cotransfected with the AnnexinA2 siRNA. We first transfected Panc10.05 tumor cells with either: the control pcDNA vector, the pcDNA plasmid expressing FLAG-tagged wild-type AnnexinA2 (ANXA2 WT-FLAG), Y23A-mutated AnnexinA2 (ANXA2Y23A-FLAG), or Y23E-mutated AnnexinA2 (ANXA2Y23E-FLAG). As shown in FIG. 11A, FLAG-tagged AnnexinA2 expression from all three constructs is detected in the cytoplasm, whereas only ANXA2 WT-FLAG and Y23E mutated AnnexinA2 localizes to the cell membrane fraction. Importantly, only ANXA2 WT-FLAG becomes tyrosine phosphorylated in the cell membrane fraction. Next, we co-transfected the cells with the siRNA duplex that specifically targets only endogenous AnnexinA2. As shown in FIG. 11B, transfection with the empty pcDNA vector had no effect on the in vitro invasion of Panel 0.05 cells. However, transfection with either ANXA2 WT-FLAG or ANXA2Y23E-FLAG had a dominant negative effect on the invasion of Panel 0.05 cells. Interestingly, transfection with ANXA2Y23A-FLAG further inhibited the invasion of Panc10.05 cells, and co-transfection of the empty vector with the AnnexinA2 targeting siRNA inhibited invasion to the same extent. By contrast, co-transfection of the pcDNA plasmid expressing ANXA2WT-FLAG or ANXA2Y23E-FLAG reversed the siRNA mediated inhibition of invasion. Nonetheless, co-transfection of the pcDNA plasmid expressing ANXA2Y23A-FLAG was unable to reverse the siRNA mediated inhibition of invasion. Taken together, these data provide strong support that Try23 phosphorylation of AnnexinA2 is essential for the invasion of PDAC cells.

Example 14—AnnexinA2 Plays a Role in the Epithelial-Mesenchymal Transition

The initial step of invasion-metastasis mimics Epithelial-Mesenchymal Transition (EMT), a normal morphogenic process during embryonic development (Weinberg 2008). AnnexinA2 has been shown to mediate TGFβ-activated EMT during the process of cardiac valve development (Krishnan, Deora et al. 2004). It has been repeatedly shown that TGFβ can induce EMT in cultured PDAC cells (Gordon, Dong et al. 2008; Zhao, Venkatasubbarao et al. 2008). In addition, previous studies have demonstrated that EMT mediates invasion and metastases of PDAC (Zhao, Venkatasubbarao et al. 2008). Therefore, we hypothesized that AnnexinA2 may play a key role in mediating the EMT process during PDAC invasion and metastasis. EMT is characterized by a typical transcription circuit of events. The transcription of epithelial markers such as E-cadherin are suppressed and that of mesenchymal markers such as slug and vimentin are induced. To examine the role of AnnexinA2 in the EMT process of PDAC cells, we employed a lentiviral vector containing AnnexinA2 siRNA as a method to achieve long-term suppression of AnnexinA2. Panc10.05 cells infected with this lentivirus were FACS-sorted by GFP, which was co-expressed by the lentivirus. Following the sort, we confirmed that expression of AnnexinA2 was stably knocked down in the siRNA-lentiviral infected cells (data not shown). Next, GFP-sorted siRNA-lentiviral infected cells were subjected to real-time RT-PCR analysis to measure the mRNA expression of E-cadherin, slug, and vimentin. As a negative control, the lentivirus expressing only GFP was also used to infect a control population of Panc10.05 cells. These cells were also sorted for GFP-positive cells. One pair of Panc10.05 cell lines, with and without AnnexinA2 siRNA, were treated with TGFβ for 48 hours before they were harvested for mRNA expression analysis. The real-time PCR analysis showed that the epithelial marker E-cadherin was suppressed and that both mesenchymal markers, slug and vimentin, were induced during the TGFβ-induced EMT process in the control Panc10.05 cells without AnnexinA2 siRNA. By contrast, E-cadherin was not suppressed and slug or vimentin expression were not induced by the TGFβ treatment in the Panc10.05 cells where AnnexinA2 was knocked down by siRNA. This result demonstrates that loss of AnnexinA2 expression leads to loss of TGFβ-induced EMT in PDAC cells. These data therefore provide a mechanism to explain why loss of AnnexinA2 inhibits the invasion capacity of PDAC cells.

Example 15—Methods and Materials for Examples 8-14

Cell Lines and Tissue Culture

The human pancreatic cancer cell lines except MiaPaca-2 were previously established by the Johns Hopkins pancreatic tumor GI SPORE research program (Jones, Zhang et al. 2008). MiaPaca-2 was originally obtained from the American Type Culture Collection. The human fibroblast cell line was established from paracancerous tissues of human pancreatic adenocarcinoma. All cell lines were maintained in the RPMI1640 media supplemented with 10% fetal bovine serum and grown in a humidified incubator at 37° C. and 5% $CO_2$. As indicated, TGFβ1 (R&D Systems) were added in the culture medium at a final concentration of 400 pM. Cells were treated by TGFβ1 for 48 hours before harvest.

Human Serum and Antibodies

Human serum was obtained from the patients enrolled in the phase II pancreatic vaccine adjuvant study by following the IRB-approved protocol (Lutz et al. Manuscript submitted). Serum was collected and stored according to standard procedures (Jaffee, Hruban et al. 2001). Rabbit polyclonal anti-AnnexinA2 antibodies (H50) were obtained from Santa Cruz Biotechnology, Inc.

DNA Cloning and Plasmid Constructions

The full-length human AnnexinA2 cDNA was obtained by reverse transcription of total RNA purified from Panel 0.05 cells, followed by high-fidelity PCR amplification with the AnnexinA2 primers. The non-complementary region of the reverse primer also contained the sequence of FLAG tag. The resultant PCR product of the AnnexinA2 cDNA was then cloned into the pCR vector (Invitrogen) and was sequenced to confirm no introduction of missense or nonsense mutations. Then, the AnnexinA2 cDNA fragment with a C-terminal FLAG tag was further subcloned into the lentiviral vector (LV). In this lentivirus, AnnexinA2 is expressed under the control of the EF-1☐ promoter. In addition, for the cotransfection of both plasmids and siRNA, the resultant PCR product of the AnnexinA2 cDNA with a C-terminal FLAG tag was cloned into the pcDNA3.3 vector (Invitrogen) directly. Y23A and Y23E mutations were created by the site-directed mutagenesis according to the manufacturer's manual (Stratagene).

Plasmid Transfection, Lentiviral Infection, and RNA Interference

For plasmid transfection and RNA interference, cells were seeded in multiple 6-well plates to 80% confluence. For each well, 2 ☐g of pcDNA-based plasmid and/or 40 pmol siRNA duplex, were transfection with the lipofectamine 2000 reagent in a serum-containing medium according to the manufacturer's manual (Invitrogen). For protein expression analysis, cells were harvested in 48 hours. For in vitro invasion assay, cells were starved in serum-free media for another 24 hours. The AnnexinA2 siRNA was synthesized by Ambien, Inc.; and the scramble siRNA was also purchased from Ambion.

To produce lentivirus expressing AnnexinA2, the plasmid with lentiviral constructs was co-transfected with packaging plasmids into 293T cells as previously described (Zhou, Cui et al. 2003). Lentivirus supernatant was collected at 48 hours. For infection, cells were seeded in multiple 6-well plates to 80% confluence. For each well, 2 ml lentivirus supernatant was added and incubated for 48 hours before the cells were harvested.

The lentivirus expressing hairpin siRNA of AnnexinA2 was obtained from Open Biosystems. Lentivirus was produced according to the manufacturer's manual. For infection of Panel 0.05 cells, 6 milliliters of viral supernatant was added to adherent cells plated in each 75 cm flask and incubated for 48 hours. Cells from two flasks were sorted by GFP in a FACS cell sorter at approximately 72-96 hours after infection. The cells infected with lentivirus expressing GFP alone were sorted similarly. Total RNA was immediately extracted after cell sorting.

Cell Invasion Assays

Cell invasion assays were carried out using the 96-well Transwell plates with 8-μm pores and reagents in the Cultrex BME Cell Invasion Assay system according to the manufacturer's manual with modification (R&D Systems). In an invasion experiment, 1×BME (Basement Membrane Extract) was used to coat the top well and 10% serum containing media were added to the bottom well. To score the cells across the transwell, MTT (3-(4,5-Dimethylthiazol-2-yl)-2,5-diphenyltetrazolium bromide) assays were used as previously described (Imamura, Takao et al. 1994). Relative MTT units representing the invasion capacity were measured and normalized by cell numbers. To assess the spontaneous leakage of cells through the BME-coated transwell, invasion specificity controls were also performed by only adding serum-free media in the bottom wells. To exclude the effect of such leakage, relative MTT units in the invasion experiments are adjusted by subtracting the MTT values of leaked cells in matched invasion specificity controls.

Fluorescent Immunostaining

Panc10.05 cells grew on cover slips to 90% confluence and were fixed in 4% paraformaldehyde for 15 min. Cover slips were then incubated with PBS containing 0.1% Triton X-100 for 5 minutes followed by washing with PBS. After cover slips were blocked with 10% normal goat sera in PBS for one hour, they were incubated with rabbit anti-AnnexinA2 antibodies at a 1:100 dilution in 10% normal goat sera overnight at 4° C. Following a PBS wash, they were further incubated with FITC-conjugated goat anti-rabbit IgG (Santa Cruz Biotechnology) at a 1:200 dilution in 10% normal goat sera at room temperature for 1 hour. They were subsequently washed with PBS containing 0.5% NP-40. Finally, the cover slips were mounted in a medium containing DAPI (4',6-diamidino-2-phenylindole) (Vector Labs) and examined by a fluorescent microscope.

Immunohistochemistry

Human pancreatic tissue samples were obtained in accordance with a JHMI IRB-approved protocol. Immunohistochemical staining for AnnexinA2 was performed using a standard protocol on automated stainer from Leica Microsystems. After deparaffinization and hydration of tissue, heat induced antigen retrieval was performed with EDTA buffer (pH 9.0) for 20 minutes. Incubation with the H50 rabbit anti-AnnexinA2 antibodies (Santa Cruz Biotechnology) at a 1:100 dilution was followed by secondary antibody incubation from bond polymer refine detection kit (Leica Microsystems). The reaction was developed by using substrate 3,3'-Diamino-benzidine hydrochloride (DAB). All Slides were counterstained with hematoxylin. Each area of PDAC cells on the entire slide will be scored from 0 to 3 by clinical pathologists. Scores of 0 to 3 measure the different intensities of cell-surface staining of AnnexinA2, with a score of 0 representing no staining and a score of 3 representing the strongest staining. The percentage of PDAC cells at each score level will be estimated. The average score of cell-surface AnnexinA2 expression is calculated as follows:

$$\text{Average Score} = 0 \times a\% + 1 \times b\% + 2 \times c\% + 3 \times d\%$$

(a %, b %, c %, and d % are the percentages of PDAC cells with score 0 to 3, respectively.)

Whole Cell Extract and Cell Fractionation

The whole cell extract of pancreatic cancer cells was obtained as previously described (Chen, Riley et al. 1997). In brief, cell pellets were resuspended in the Lysis 250 buffer followed by a freeze and thaw process that was performed three times. The cell lysate was spun at 15,000 rpm for 10 min and the supernatent was removed. The protocols to separate membrane and cytoplasmic fractions were adapted from those previously published (Abrams, Rohrschneider et al. 1982). EGTA (Ethylene glycol-bis(2-aminoethylether)-N,N,N',N'-tetraacetic acid) elution of cell surface AnnexinA2 followed a previously established procedure (Deora, Kreitzer et al. 2004).

Immunoprecipitation and Immunoblot Analysis

Anti-phosphotyrosine antibody conjugated sepharose (P-Try-100, Cell Signaling Technology) was used to immunprecipate tyrosine-phosphorylated proteins. Anti-AnnexinA2 antibodies and anti-FLAG M2 antibodies (Sigma) were first conjugated to sepharose beads according to the manufacturer's manual (Pierce) prior to being used for immunoprecipation. All immunoprecipations were done at 40 C for overnight, followed by washing with the Lysis 250 buffer (Chen, Riley et al. 1997).

After whole cell extracts, cell fractions, or immunoprecipitants were boiled in SDS-sampling buffer, they were loaded on 10% gradient SDS-PAGE (BioRad). The gel was then transferred to the membrane and blotted with rabbit anti-AnnexinA2 polyclonal antibodies in 1:1000 dilution followed by HRP-conjugated goat anti-rabbit IgG (Amershan Pharmacia) at a 1:3000 dilution.

Recombinant His6-tagged AnnexinA2 was expressed in TOP10 *E. coli* and purified on a High-Trap Ni column according to the manufacturer's manual (Amershan Pharmacia). One microgram of purified His6-tagged AnnexinA2 was loaded on each well of a 10% gradient SDS-PAGE. After transferring to the membrane, each individual lane was blotted with either pre-vaccination serum or post-vaccination serum at a 1:1000 dilution. Mouse anti-human IgG antibody (Sigma) was used as a 1:5000 dilution as the secondary antibody.

Reverse Transcription and Real-Time PCR

RNA was isolated from cells using the RNAEasy kit (Qiagen), reverse transcribed using the first strand cDNA synthesis kit (Invitrogen). Quantitative real-time reverse transcription-PCR (qRT-PCR) was performed with gene-specific fluorescent TaqMan probes (Applied Biosystems) using an ABI PRISM 7500 Sequence Detection System Instrument and the associated software (Applied Biosystems) following the manufacturer's instructions. Each reaction was performed in triplicate at two cDNA dilutions. The standard human β-actin gene (BACT; Applied Biosystems) was used to normalize variations in the quantities of input cDNA.

REFERENCES

The disclosure of each reference cited is expressly incorporated herein.

For examples 1-7 and other numbered references in the text.

1. Groom J, Mackay F. 2008. B cells flying solo. *Immunol Cell Biol.* 86: 40-46.
2. Bei R, Masuelli L, Palumbo C, Modesti M, Modesti A. 2009. A common repertoire of autoantibodies is shared by cancer and autoimmune disease patients: Inflammation in their induction and impact on tumor growth. *Cancer Lett.* 281:8-23.
3. Preiss S, Kammertoens T, Lampert C, Willimsky G, Blankenstcin T. 2005. Tumor-induced antibodies resemble the response to tissue damage. *Int J. Cancer.* 115:456-462.
4. Barua A, Edassery S L, Bitterman P, Abramowicz J S, Dirks A L, Bahr J M, Hales D B, Bradaric M J, Luborsky J L. 2009. Prevalence of antitumor antibodies in laying hen model of human ovarian cancer. *Int J Gynecol Cancer.* 19:500-507.
5. Carey T E, Takahashi T, Resnick L A, Oettgen H F, Old L J. 1976. Cell surface antigens of human malignant melanoma: mixed hemadsoiption assays for humoral immunity to cultured autologous melanoma cells. *Proc Natl Acad Sci USA.* 73:3278-3282.
6. Garrett T J, Takahashi T, Clarkson B D, Old L J. 1977. Detection of antibody to autologous human leukemia cells by immune adherence assays. *Proc Natl Acad Sci USA.* 74:4587-4590.
7. Pfreundschuh M, Shiku H, Takahashi T, Ueda R, Ransohoff J, Oettgen H F, Old L J. 1978. Serological analysis of cell surface antigens of malignant human brain tumors. *Proc Natl Acad Sci USA.* 75:5122-5126.
8. Ueda R, Shiku H, Pfreundschuh M, Takahashi T, Li L T, Whitmore W F, Oettgen H F, Old L J. 1979. Cell surface antigens of human renal cancer defined by autologous typing. *J Exp Med.* 150:564-579.
9. Old L J. 1981. Cancer immunology: the search for specificity—G. H. A. Clowes Memorial lecture. *Cancer Res.* 41: 361-375.
10. Livingston P O, Natoli E J, Calves M J, Stockert E, Oettgen H F, Old U. 1987. Vaccines containing purified GM2 ganglioside elicit GM2 antibodies in melanoma patients. *Proc Natl Acad Sci USA.* 84:2911-2915.
11. Kitamura K, Livingston P O, Fortunato S R, Stockert E, Helling F, Ritter G, Oettgen H F, Old L J. 1995. Serological response patterns of melanoma patients immunized with a GM2 ganglioside conjugate vaccine. *Proc Natl Acad Sci USA.* 92:2805-2809.
12. Livingston P O, Wong G Y, Adluri S, Tao Y, Padavan M, Parente R, Hanlon C, Calves M J, Helling F, Ritter G, Oettgen H F, Old L J. 1994. Improved survival in stage III melanoma patients with GM2 antibodies: a randomized trial of adjuvant vaccination with GM2 ganglioside. *J Clin Oncol.* 12:1036-1044.
13. Ludwig Institute for Cancer Research, Academy of Cancer Immunology, European Cancer Immunome Program. ludwig-sun5.unil.ch/CancerImmunomeDB
14. Soussi T. 2000. p53 Antibodies in the sera of patients with various types of cancer: a review. *Cancer Res.* 60:1777-1788.
15. Jäger E, Stockert E, Zidianakis Z, Chen Y T, Karbach J, Jäger D, Arand M, Ritter G, Old L J, Knuth A. 1999. Humoral immune responses of cancer patients against "Cancer-Testis" antigen NY-ESO-1: correlation with clinical events. *Int J. Cancer.* 84:506-510.
16. Yagihashi A, Asanuma K, Nakamura M, Araya J, Mano Y, Torigoe T, Kobayashi D, Watanabe N. 2001. Detection of anti-survivin antibody in gastrointestinal cancer patients. *Clin Chem.* 47:1729-1731.
17. Eto M, Kodama S, Uemura N, Suzuki M. 2007. Antibody responses to survivin and their clinical significance in patients with head and neck cancer. *Head Neck* 29:1128-1135.
18. Disis M L, Pupa S M, Gralow J R, Dittadi R, Menard S, Cheever M A. 1997. High-titer HER-2/neu protein-specific antibody can be detected in patients with early-stage breast cancer. *J Clin Oncol.* 15:3363-3367.
19. von Mensdorff-Pouilly S, Verstraeten A A, Kenemans P, Snijdewint F G, Kok A, Van Kamp G J, Paul M A, Van Diest P J, Meijer S, Hilgers J. 2000. Survival in early breast cancer patients is favorably influenced by a natural humoral immune response to polymorphic epithelial mucin. *J Clin Oncol.* 18:574-583.
20. Hamanaka Y, Suchiro Y, Fukui M, Shikichi K, Imai K, Hinoda Y. 2003. Circulating anti-MUC1 IgG antibodies as a favorable prognostic factor for pancreatic cancer. *Int J. Cancer.* 103:97-100.
21. Davis I D, Chen W, Jackson H, Parente P, Shackleton M, Hopkins W, Chen Q, Dimopoulos N, Luke T, Murphy R, Scott A M, Maraskovsky E, McArthur G, MacGregor D, Sturrock S, Tai T Y, Green S, Cuthbertson A, Maher D, Miloradovic L, Mitchell S V, Ritter G, Jungbluth A A, Chen Y T, Gnjatic S, Hoffman E W, Old L J, Cebon J S. 2004. Recombinant NY-ESO-1 protein with ISCOMA-TRIX adjuvant induces broad integrated antibody and CD4 (+) and CD8 (+) T cell responses in humans. Proc Natl Acad Sci USA. 101:10697-10702.
22. Jäger E, Karbach J, Gnjatic S, Neumann A, Bender A, Valmori D, Ayyoub M, Ritter E, Ritter G, Jäger D, Panicali D, Hoffman E, Pan L, Oettgen H, Old L J, Knuth A. 2006. Recombinant vaccinia/fowlpox NY-ESO-1 vaccines induce both humoral and cellular NY-ESO-1-specific immune responses in cancer patients. *Proc Nall Acad Sci USA.* 103:14453-14458.
23. Tang C K, Katsara M, Apostolopoulos V. 2008. Strategies used for MUC1 immunotherapy: human clinical studies. *Expert Rev Vaccines.* 7:963-975.
24. Dranoff G, Jaffee E, Lazenby A, Golumbek P, Levitsky H, Brose K, Jackson V, Hamada H, Pardoll D, Mulligan R C. 1993. Vaccination with irradiated tumor cells engineered to secrete murine granulocyte-macrophage colony-stimulating factor stimulates potent, specific, and long-lasting anti-tumor immunity. *Proc Natl Acad Sci USA.* 90: 3539-3543.
25. Simmons A D, Li B, Gonzalez-Edick M, Lin C, Moskalenko M, Du T, Creson J, VanRoey M J, Jooss K. 2007. GM-CSF-secreting cancer immunotherapies: preclinical analysis of the mechanism of action. *Cancer Immunol Immunother.* 56:1653-1665.
26. Li B, VanRoey M, Triebel F, Jooss K. 2008. Lymphocyte activation gene-3 fusion protein increases the potency of a granulocyte macrophage colony-stimulating factor-secreting tumor cell immunotherapy. *Clin Cancer Res.* 14:3545-3554
27. Fonseca C, Soiffer R, Ho V, Vanneman M, Jinushi M, Ritz J, Neuberg D, Stone R, DeAngelo D, Dranoff G. 2009. Protein disulfide isomerases are antibody targets during immune-mediated tumor destruction. *Blood.* 113: 1681-1688.
28. Lutz E R, Biedrzycki B, Kobrin B, Herman J, Sugar E, Yeo C J, Piantadosi S, Cameron J L, Lillemoe K, Solt S, Onners B, Tartakovsky I, Choi M, Sharma R, Illei P B, Hruban R H, Abrams R, Le D, Jaffee E, Laheru D. 2009. A lethally irradiated allogeneic granulocyte-macrophage colony stimulating factor-secreting tumor vaccine for pancreatic adenocarcinoma: A phase II trial of safety, efficacy, and immune activation. (submitted)
29. Vishwanatha J K, Chiang Y, Kumble K D, Hollingsworth M A, Pour P M. 1993. Enhanced expression of annexin II in human pancreatic carcinoma cells and primary pancreatic cancers. *Carcinogenesis.* 14:2575-2579.
30. Altenberg B, Greulich K O. 2004. Genes of glycolysis are ubiquitously overexpressed in 24 cancer classes. *Genomics.* 84:1014-1020.
31. Cappello F, de Macario E C, Marasà. L, Zummo G, Macario A J. 2008. Hsp60 expression, new locations, functions and perspectives for cancer diagnosis and therapy. *Cancer Biol Ther.* 7:801-809.
32. Chen J H, Ni R Z, Xiao M B, Guo J G, Zhou J W. 2009. Comparative proteomic analysis of differentially expressed proteins in human pancreatic cancer tissue. *Hepatobiliary Pancreat Dis Int.* 8:193-200.
33. Zhao L, Wang H, Li J, Liu Y, Ding Y. 2008. Overexpression of Rho GDP-dissociation inhibitor alpha is associated with tumor progression and poor prognosis of colorectal cancer. *J Proteome Res.* 7:3994-4003.
34. Kiewe P, Wojtke S, Thiel E, Nagorsen D. 2009. Antiviral cellular immunity in colorectal cancer patients. *Hum Immunol.* 70:85-88.
35. Montero E, Valdes M, Avellanet J, Lopez A, Perez R, Lage A. 2009. Chemotherapy induced transient B-cell depletion boosts antibody-forming cells expansion driven by an epidermal growth factor-based cancer vaccine. *Vaccine.* 27:2230-2239.
36. Dumic J, Dabelic S, Flogel M. 2006. Galectin-3: an open-ended story. *Biochim Biophys Acta.* 1760:616-635.
37. Nakahara S, Raz A. 2007. Regulation of cancer-related gene expression by galectin-3 and the molecular mechanism of its nuclear import pathway. *Cancer Metastasis Rev.* 26:605-610.
38. Miranda F A, Hassumi M K, Guimarães MC, Simões R T, Silva T G, Lira R C, Rocha A M, Mendes C T Jr, Donadi E A, Soares C P, Soares E G. 2009. Galectin-3 overexpression in invasive laryngeal carcinoma, assessed by computer-assisted analysis. *J Histochem Cytochem.* 57:665-673.
39. Nangia-Makker P, Balan V, Raz A. 2008. Regulation of tumor progression by extracellular galectin-3. *Cancer Microenviron.* 1:43-51.
40. Takenaka Y, Fukumori T, Raz A. 2004. Galectin-3 and metastasis. *Glycoconj J.* 19:543-549.
41. Demotte N, Stroobant V, Courtoy P J, Van Der Smissen P, Colau D, Luescher I F, Hivroz C, Nicaise J, Squifflet J L, Mourad M, Godelaine D, Boon T, van der Bruggen P. 2008. Restoring the association of the T cell receptor with CD8 reverses anergy in human tumor-infiltrating lymphocytes. *Immunity.* 28:414-424.
42. Chen H Y, Fermin A, Vardhana S, Weng I C, Lo K F, Chang E Y, Maverakis E, Yang R Y, Hsu D K, Dustin M L, Liu F T. 2009. Galectin-3 negatively regulates TCR-mediated CD4+ T-cell activation at the immunological synapse. *Proc Natl Acad Sci USA.* 106:14496-14501.
43. Lin C I, Whang E E, Donner D B, Jiang X, Price B D, Carothers A M, Delaine T, Leffler H, Nilsson U J, Nose V, Moore F D Jr, Ruan D T. 2009. Galectin-3 targeted therapy with a small molecule inhibitor activates apoptosis and enhances both chemosensitivity and radiosensitivity in papillary thyroid cancer. *Mol Cancer Res.* 7 (10): online first.
44. Glinsky V V, Kiriakova G, Glinskii O V, Mossine V V, Mawhinney T P, Turk J R, Glinskii A B, Huxley V H, Price J E, Glinsky G V. 2009. Synthetic galectin-3 inhibitor increases metastatic cancer cell sensitivity to taxol-induced apoptosis in vitro and in vivo. *Neoplasia.* 11:901-9.
45. Esposito I, Penzel R, Chaib-Harrireche M, Barcena U, Bergmann F, Riedl S, Kayed H, Giese N, Kleeff J, Friess H, Schirmacher P. 2006. Tenascin C and annexin II expression in the process of pancreatic carcinogenesis. *J. Pathol.* 208:673-685.
46. Mikuriya K, Kuramitsu Y, Ryozawa S, Fujimoto M, Mori S, Oka M, Hamano K, Okita K, Sakaida I, Nakamura K. 2007. Expression of glycolytic enzymes is increased in pancreatic cancerous tissues as evidenced by proteomic profiling by two-dimensional electrophoresis and liquid chromatography-mass spectrometry/mass spectrometry. *Int J. Oncol.* 30:849-855.
47. Piselli P, Vendetti S, Vismara D, $C_1$_cconi R, Poccia F, Colizzi V, Delpino A. 2000. Different expression of CD44, ICAM-1, and HSP60 on primary tumor and metastases of a human pancreatic carcinoma growing in scid mice. *Anticancer Res.* 20:825-831.

48. Li Z, Chang Z, Chiao L J, Kang Y, Xia Q, Zhu C, Fleming J B, Evans D B, Chiao P J. 2009. TrkBT1 induces liver metastasis of pancreatic cancer cells by sequestering Rho GDP dissociation inhibitor and promoting RhoA activation. *Cancer Res.* 69:7851-7859.
49. Ortiz-Zapater E, Peiro S, Roda O, Corominas J M, Aguilar S, Ampurdanes C, Real F X, Navarro P. 2007. Tissue plasminogen activator induces pancreatic cancer cell proliferation by a non-catalytic mechanism that requires extracellular signal-regulated kinase ½ activation through epidermal growth factor receptor and AnnexinA2. *Am J Pathol.* 170:1573-1584.
50. Miles L A, Dahlberg C M, Plescia J, Felez J, Kato K, Plow E F. 1991. Role of cell-surface lysines in plasminogen binding to cells: identification of alpha-enolase as a candidate plasminogen receptor. *Biochemistry*. 30:1682-1691.
51. Hamaguchi T, Iizuka N, Tsunedomi R, Hamamoto Y, Miyamoto T, Iida M, Tokuhisa Y, Sakamoto K, Takashima M, Tamesa T, Oka M. 2008. Glycolysis module activated by hypoxia-inducible factor 1α is related to the aggressive phenotype of hepatocellular carcinoma. *Int J. Oncol.* 33:725-731.
52. Barazi H O, Zhou L, Templeton N S, Krutzsch H C, Roberts D D. 2002. Identification of heat shock protein 60 as a molecular mediator of alpha 3 beta 1 integrin activation. *Cancer Rev.* 62:1541-1548.
53. Tsuji T. 2004. Physiological and pathological roles of alpha3beta1 integrin. *J Membr Biol.* 200:115-132.
54. DerMardirossian C, Bokoch G M. 2005. GDIs: central regulatory molecules in Rho GTPase activation. *Treands Cell Biol.* 15:356-363.
55. Takano S, Togawa A, Yoshitomi H, Shida T, Kimura F, Shimizu H, Yoshidome H, Ohtsuka M, Kato A, Tomonaga T, Nomura F, Miyazaki M. 2008. Annexin II overexpression predicts rapid recurrence after surgery in pancreatic cancer patients undergoing gemcitabine-adjuvant chemotherapy. *Ann Surg Oncol.* 15:3157-3168.
56. Zhao L, Wang H, Li J, Liu Y, Ding Y. 2008. Overexpression of Rho GDP-dissociation inhibitor alpha is associated with tumor progression and poor prognosis of colorectal cancer. *J Proteome Res.* 7:3994-4003.
57. Morse M A, Hall J R, Plate J M. 2009. Countering tumor-induced immunosuppression during immunotherapy for pancreatic cancer. Expert Opin Biol Ther. 9:331-339.
58. Suzuki E, Kapoor V, Jassar A S, Kaiser L R, Albelda S M. 2005. Gemcitabine selectively eliminates splenic Gr-1+/CD11b+ myeloid suppressor cells in tumor-bearing animals and enhances antitumor immune activity. *Clin Cancer Res.* 11:6713-6721.
59. Lutsiak M E, Semnani R T, De Pascalis R, Kashmiri S V, Schlom J, Sabzevari H.2005. Inhibition of CD4+25+ T regulatory cell function implicated in enhanced immune response by low-dose cyclophosphamide. Blood. 105: 2862-2868.
60. Bang S, Kim H S, Choo Y S, Park S W, Chung J B, Song S Y. 2006. Differences in immune cells engaged in cell-mediated immunity after chemotherapy for far advanced pancreatic cancer. *Pancreas.* 32:29-36.
61. Shebzukhov Y V, Koroleva E P, Khlgatian S V, Lagarkova M A, Meshcheryakov A A, Lichinitser M R, Karbach J, Jager E, Kuprash D V, Nedospasov S A. 2005. Humoral immune response to thymidylate synthase in colon cancer patients after 5-FU chemotherapy. *Immunol Lett.* 100:88-93.
62. Jaffee E M, Schutte M, Gossett J, Morsberger L A, Adler A J, Thomas M, Greten T F, Hruban R H, Yeo C J, Griffin C A. 1998. Development and characterization of a cytokine-secreting pancreatic adenocarcinoma vaccine from primary tumors for use in clinical trials. *Cancer J Sci Am.* 4:194-203.
63. Ilyinskii P O, Gambaryan A S, Meriin A B, Gabai V, Kartashov A, Thoidis G, Shneider A M. 2008. Inhibition of influenza M2-induced cell death alleviates its negative contribution to vaccination efficiency. *PLoS One.* 3 (1): e1417. For examples 8-15 and other author-referenced citations in the text.

REFERENCE

Abrams, H. D., L. R. Rohrschneider, et al. (1982). "Nuclear location of the putative transforming protein of avian myelocytomatosis virus." *Cell* 29 (2): 427-39.

Argani, P., C. Iacobuzio-Donahue, et al. (2001). "Mesothelin is overexpressed in the vast majority of ductal adenocarcinomas of the pancreas: identification of a new pancreatic cancer marker by serial analysis of gene expression (SAGE)." *Clin Cancer Res* 7 (12): 3862-8.

Chen, Y., D. J. Riley, et al. (1997). "HEC, a novel nuclear protein rich in leucine heptad repeats specifically involved in mitosis." *Mol Cell Biol* 17 (10): 6049-56.

Deora, A. B., G. Kreitzer, et al. (2004). "An annexin 2 phosphorylation switch mediates p11-dependent translocation of annexin 2 to the cell surface." *J Biol Chem* 279 (42): 43411-8.

Esposito, I., R. Penzel, et al. (2006). "Tenascin C and annexin II expression in the process of pancreatic carcinogenesis." *J Pathol* 208 (5): 673-85.

Goggins, M., S. E. Kern, et al. (1999). "Progress in cancer genetics: lessons from pancreatic cancer." *Ann Oncol* 10 Suppl 4: 4-8.

Gordon, K. J., M. Dong, et al. (2008). "Loss of type III transforming growth factor beta receptor expression increases motility and invasiveness associated with epithelial to mesenchymal transition during pancreatic cancer progression." *Carcinogenesis* 29 (2): 252-62.

Hassan, R. and M. Ho (2008). "Mesothelin targeted cancer immunotherapy." *Eur J Cancer* 44 (1): 46-53.

Hastie, C., J. R. Masters, et al. (2008). "Interferon-gamma reduces cell surface expression of annexin 2 and suppresses the invasive capacity of prostate cancer cells." *J Biol Chem* 283 (18): 12595-603.

Hingorani, S. R., L. Wang, et al. (2005). "Trp53R172H and KrasG12D cooperate to promote chromosomal instability and widely metastatic pancreatic ductal adenocarcinoma in mice." *Cancer Cell* 7 (5): 469-83.

Hotz, B., M. Arndt, et al. (2007). "Epithelial to mesenchymal transition: expression of the regulators snail, slug, and twist in pancreatic cancer." *Clin Cancer Res* 13 (16): 4769-76.

Irnamura, H., S. Takao, et al. (1994). "A modified invasion-3-(4,5-dimethylthiazole-2-yl)-2,5-diphenyltetrazolium bromide assay for quantitating tumor cell invasion." *Cancer Res* 54 (13): 3620-4.

Jaffee, E. M., R. H. Hruban, et al. (2001). "Novel allogeneic granulocyte-macrophage colony-stimulating factor-secreting tumor vaccine for pancreatic cancer: a phase I trial of safety and immune activation." *J Clin Oncol* 19 (1): 145-56.

Jones, S., X. Zhang, et al. (2008). "Core signaling pathways in human pancreatic cancers revealed by global genomic analyses." *Science* 321 (5897): 1801-6.

Kim, J. and K. A. Hajjar (2002). "Annexin II: a plasminogen-plasminogen activator co-receptor."*Front Biosci* 7: d341-8.

Krishnan, S., A. B. Deora, et al. (2004). "Annexin II-mediated plasmin generation activates TGF-beta3 during epithelial-mesenchymal transformation in the developing avian heart." *Dev Biol* 265 (1): 140-54.

Kwon, M., T. J. MacLeod, et al. (2005). "S100A10, AnnexinA2, and AnnexinA2 heterotetramer as candidate plasminogen receptors." *Front Biosci* 10: 300-25.

Laheru, D., E. Lutz, et al. (2008). "Allogeneic granulocyte macrophage colony-stimulating factor-secreting tumor immunotherapy alone or in sequence with cyclophosphamide for metastatic pancreatic cancer: a pilot study of safety, feasibility, and immune activation." *Clin Cancer Res* 14 (5): 1455-63.

Liu, J., C. A. Rothermund, et al. (2003). "Nuclear annexin II negatively regulates growth of LNCaP cells and substitution of ser 11 and 25 to glu prevents nucleo-cytoplasmic shuttling of annexin II." *BMC Biochem* 4: 10.

Lu, G., H. Maeda, et al. (2006). "Cloning and characterization of the annexin II receptor on human marrow stromal cells." *J Biol Chem* 281 (41): 30542-50.

Massey-Haarroche, D., N. Mayran, et al. (1998). "Polarized localizations of annexins I, II, VI and XIII in epithelial cells of intestinal, hepatic and pancreatic tissues." *J Cell Sci* 111 (Pt 20): 3007-15.

Merrifield, C. J., U. Rescher, et al. (2001). "Annexin 2 has an essential role in actin-based macropinocytic rocketing." *Curr Biol* 11 (14): 1136-41.

Natalwala, A., R. Spychal, et al. (2008). "Epithelial-mesenchymal transition mediated tumourigenesis in the gastrointestinal tract." *World J Gastroenterol* 14 (24): 3792-7.

Pierantoni, C., A. Pagliacci, et al. (2008). "Pancreatic cancer: progress in cancer therapy." *Crit. Rev Oncol Hematol* 67 (1): 27-38.

Rescher, U. and V. Gerke (2004). "Annexins—unique membrane binding proteins with diverse functions." *J Cell Sci* 117 (Pt 13): 2631-9.

Sharma, M. C. and M. Sharma (2007). "The role of annexin II in angiogenesis and tumor progression: a potential therapeutic target." *Curr Pharm Des* 13 (35): 3568-75.

Singh, P. (2007). "Role of Annexin-II in GI cancers: interaction with gastrins/progastrins."*Cancer Lett* 252 (1): 19-35.

Strimpakos, A., M. W. Saif, et al. (2008). "Pancreatic cancer: from molecular pathogenesis to targeted therapy." *Cancer Metastasis Rev* 27 (3): 495-522.

Thomas, A. M., L. M. Santarsiero, et al. (2004). "Mesothelin-specific CD8 (+) T cell responses provide evidence of in vivo cross-priming by antigen-presenting cells in vaccinated pancreatic cancer patients." *J Exp Med* 200 (3): 297-306.

Vishwanatha, J. K., Y. Chiang, et al. (1993). "Enhanced expression of annexin II in human pancreatic carcinoma cells and primary pancreatic cancers." *Carcinogenesis* 14 (12): 2575-9.

Weinberg, R. A. (2008). "Twisted epithelial-mesenchymal transition blocks senescence." *Nat Cell Biol* 10 (9): 1021-3.

Wolff, A. C., M. E. Hammond, et al. (2007). "American Society of Clinical Oncology/College of American Pathologists guideline recommendations for human epidermal growth factor receptor 2 testing in breast cancer." *J Clin Oncol* 25 (1): 118-45.

Zhao, S., K. Venkatasubbarao, et al. (2008). "Inhibition of STAT3 Tyr705 phosphorylation by Smad4 suppresses transforming growth factor beta-mediated invasion and metastasis in pancreatic cancer cells." Cancer Res 68 (11): 4221-8.

Zhou, X., Y. Cui, et al. (2003). "Lentivirus-mediated gene transfer and expression in established human tumor antigen-specific cytotoxic T cells and primary unstimulated T cells." *Hum Gene Ther* 14 (11): 1089-105.

We claim:

1. A method of treating a patient with pancreatic ductal adenocarcinoma comprising:

subjecting the patient to radiotherapy and/or chemotherapy;

measuring expression of AnnexinA2 whose tyrosine 23 residue is phosphorylated on pancreatic ductal adenocarcinoma tumor cells of the patient using an anti-AnnexinA2 antibody and an anti-phosphotyrosine antibody;

administering to the patient identified as expressing the AnnexinA2, a monoclonal antibody which specifically binds to a form of AnnexinA2 whose tyrosine 23 residue is phosphorylated, and diminishing risk of tumor invasion and metastatic progression, thereby treating a patient with pancreatic ductal adenocarcinoma.

2. The method of claim 1, wherein the radiotherapy and/or chemotherapy is administered prior to and/or concomitantly with the administration of the monoclonal antibody specific for the AnnexinA2.

3. The method of claim 2, wherein the radiotherapy and/or chemotherapy is administered prior to administration of the monoclonal antibody specific for the AnnexinA2.

4. The method of claim 1, further comprising resecting the tumor.

5. A method of treating a patient with pancreatic ductal adenocarcinoma comprising:

measuring expression of AnnexinA2 having a phosphorylated tyrosine 23 residue on pancreatic ductal adenocarcinoma tumor cells of the patient using an anti-AnnexinA2 antibody and an anti-phosphotyrosine antibody;

administering to the patient identified as expressing AnnexinA2 having a phosphorylated tyrosine 23 residue, a pharmaceutical composition comprising a monoclonal antibody which specifically binds AnnexinA2, in an amount effective to diminish risk of tumor invasion and metastatic progression, thereby treating a patient with pancreatic ductal adenocarcinoma.

6. The method of claim 5, wherein the method of treatment further comprises an additional step of administering to the patient radiotherapy, chemotherapy and/or tumor resection.

* * * * *